US006455266B1

(12) United States Patent
Bulla

(10) Patent No.: US 6,455,266 B1
(45) Date of Patent: *Sep. 24, 2002

(54) **RECEPTOR FOR A *BACILLUS THURINGIENSIS* TOXIN**

(75) Inventor: Lee A. Bulla, Dallas, TX (US)

(73) Assignee: University of Wyoming, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/457,864

(22) Filed: Dec. 10, 1999

Related U.S. Application Data

(60) Division of application No. 08/880,042, filed on Jun. 20, 1997, which is a continuation-in-part of application No. 08/326,117, filed on Oct. 19, 1994, now Pat. No. 5,693,491.

(51) Int. Cl.[7] .................. G01N 33/566; C12N 15/12; C12N 5/10; C07K 14/705; C07K 14/325
(52) U.S. Cl. .................. 435/7.21; 435/7.2; 435/69.1; 435/320.1; 435/325; 435/252.3; 435/254.11; 435/7.1; 435/6; 530/300; 530/350; 536/23.1; 536/23.5; 536/23.71
(58) Field of Search ................ 435/69.1, 6, 7.1, 435/7.2, 7.4, 320.1, 325, 252.3, 254.11; 530/350, 300; 536/23.1, 23.5, 23.71

(56) References Cited

U.S. PATENT DOCUMENTS 4,675,285 A 6/1987 Clark et al.
5,071,654 A 12/1991 English

OTHER PUBLICATIONS

Oddou et al., Immunolgoically unrelated Heliothis sp. and Spodoptera sp. midgut membrane–proteins bind *Bacillus thruingeinesis* CryIA (b) delta–endotoxin, Eur. J. Biochem. 212: 145–150, 1993.*

Gill, S. S. et al. (1992) "The Mode of Action of *Bacillus thuringiensis* Endotoxins" Ammu Rev Entomol 37:615–636.

Hofte, H. et al., (1989) "Insecticidal Crystal Proteins of *Bacillus thuringiensis*" Microbiol Review 53:242–255.

Hofmann, C. et al. (1988) "Specificity of *Bacillus thuringiensis*. . ." Proc. Natl Acad Sci USA 85:7844–7848.

Ishihara, T. et al. (1991) "Molecular cloning and expression of a cDNA encoding the secretin receptor." EMBO J. 10(7):1635–1641.

Lee, M.K. et al. (1992) "Location of a Bombyx mori receptor binding region on a *Bacillus thuringiensis* delta–Endotoxins." J. Biol. Chem. 267(5):3315–3121.

Vadlamudi, R.K. et al. (1993) "A Specific Binding Protein from Manduca Sexta for the Insecticidal Toxin of *Bacillus thuringiensis* Subsp." J. Biol Chem 268(17):12334–12340.

Vadlamudi et al. (1995) Journal of Biological Chemistry 270(10): 5490–5494.

Van Rie, J. et al. (1989) "Specificity of *Bacillus thuringiensis*. . ." Eur J. Biochem 186:239–247.

Van Rie, J. et al. (1990) "Receptors on the Brush Border Membrane of the Insect Midgut as Determinants of the Specificity of *Bacillus thuringiensis*" Belta–Endotoxins Appl Environ Microbiol 56(5):1378–1385.

* cited by examiner

*Primary Examiner*—Claire M. Kaufman
(74) *Attorney, Agent, or Firm*—Morrison & Foerster LLP

(57) ABSTRACT

The cDNA that encodes a glycoprotein receptor from the tobacco hornworm which binds a *Bacillus thuringiensis* toxin has been obtained and sequenced. The availability of this cDNA permits the retrieval of DNAs encoding homologous receptors in other insects and organisms as well as the design of assays for the cytotoxicity and binding affinity of potential pesticides and the development of methods to manipulate natural and/or introduced homologous receptors and, thus, to destroy target cells, tissues and/or organisms.

11 Claims, 28 Drawing Sheets

SEQ ID NO. 1

```
          10         20         30         40
GACCAATCGGAGTGTGGTGAATTTTTGGAAAATATTTTGTGCGGTTCC
          50         60         70         80         90
TTTAGTTGTGTAATATAGTACTTTAGTTACAAATTTGGAATAATTTGG
        100        110        120        130        140
CAGCAAAACCATCTGCAGCAACAAAATCATCTGCAGCTGCGAAATCAT
          150        160        170        180        190
CTGCAGCAGCAAAAGCATCTTCAGGAGCGAGAAAAGCCCCAAATAATG
          200              210              220
TGAG    ATG  GCA  GTT  GAC  GTC  CGA  ATC  GCT  GCC  TTC
        Met  Ala  Val  Asp  Val  Arg  Ile  Ala  Ala  Phe
        230              240              250              260
CTG  CTG  GTG  TTT  ATA  GCG  CCT  GCA  GTT  TTA  GCT  CAA
Leu  Leu  Val  Phe  Ile  Ala  Pro  Ala  Val  Leu  Ala  Gln
              270              280              290
GAG  AGA  TGT  GGG  TAT  ATG  ACC  GCC  ATC  CCA  AGG  CTA
Glu  Arg  Cys  Gly  Tyr  Met  Thr  Ala  Ile  Pro  Arg  Leu
300              310              320              330
 CCA  CGA  CCG  GAT  AAT  TTG  CCA  GTA  CTA  AAT  TTT  GAA
 Pro  Arg  Pro  Asp  Asn  Leu  Pro  Val  Leu  Asn  Phe  Glu
        340              350              360              370
GGC  CAG  ACA  TGG  AGT  CAG  AGG  CCC  CTG  CTC  CCC  GCC
Gly  Gln  Thr  Trp  Ser  Gln  Arg  Pro  Leu  Leu  Pro  Ala
              380              390              400
CCG  GAG  CGG  GAT  GAC  CTG  TGC  ATG  GAC  GCC  TAC  CAC
Pro  Glu  Arg  Asp  Asp  Leu  Cys  Met  Asp  Ala  Tyr  His
        410              420              430              440
GTG  ATA  ACA  GCC  AAC  CTC  GGC  ACG  CAG  GTC  ATC  TAC
Val  Ile  Thr  Ala  Asn  Leu  Gly  Thr  Gln  Val  Ile  Tyr
              450              460              470
ATG  GAT  GAA  GAG  ATA  GAA  GAC  GAA  ATC  ACC  ATC  GCC
Met  Asp  Glu  Glu  Ile  Glu  Asp  Glu  Ile  Thr  Ile  Ala
480              490              500              510
 ATA  CTT  AAT  TAT  AAC  GGA  CCA  TCA  ACT  CCG  TTC  ATT
 Ile  Leu  Asn  Tyr  Asn  Gly  Pro  Ser  Thr  Pro  Phe  Ile
```

FIG. 1A

```
          520                 530                540              550
GAA CTG CCA TTT TTA TCC GGT TCG TAC AAT CTG CTG
Glu Leu Pro Phe Leu Ser Gly Ser Tyr Asn Leu Leu
          560                 570                580
ATG CCG GTC ATC AGG AGA GTT GAC AAC GGG GAG TGG
Met Pro Val Ile Arg Arg Val Asp Asn Gly Glu Trp
     590            600            610              620
CAT CTC ATC ATC ACG CAA AGA CAG CAT TAC GAG TTG
His Leu Ile Ile Thr Gln Arg Gln His Tyr Glu Leu
           630                640             650
CCC GGC ATG CAG CAG TAC ATG TTC AAT GTG CGC GTG
Pro Gly Met Gln Gln Tyr Met Phe Asn Val Arg Val
 660             670            680              690
 GAC GGC CAG TCG CTG GTG GCA GGC GTG TCT CTC GCT
 Asp Gly Gln Ser Leu Val Ala Gly Val Ser Leu Ala
       700            710            720              730
ATC GTC AAC ATA GAT GAC AAC GCG CCC ATC ATA CAA
Ile Val Asn Ile Asp Asp Asn Ala Pro Ile Ile Gln
           740               750            760
AAC TTC GAG CCT TGC CGG GTT CCT GAA CTG GGC GAG
Asn Phe Glu Pro Cys Arg Val Pro Glu Leu Gly Glu
     770           780            790              800
CCA GGG TTG ACA GAA TGC ACA TAC CAA GTA TCG GAC
Pro Gly Leu Thr Glu Cys Thr Tyr Gln Val Ser Asp
           810            820            830
GCG GAC GGA CGG ATC AGC ACA GAG TTC ATG ACG TTC
Ala Asp Gly Arg Ile Ser Thr Glu Phe Met Thr Phe
840            850             860            870
 AGG ATC GAC AGC GTT CGT GGC GAC GAG GAG ACC TTC
 Arg Ile Asp Ser Val Arg Gly Asp Glu Glu Thr Phe
     880            890             900            910
TAC ATC GAA CGG ACG AAT ATC CCC AAC CAA TGG ATG
Tyr Ile Glu Arg Thr Asn Ile Pro Asn Gln Trp Met
           920             930            940
TGG CTA AAT ATG ACC ATA GGC GTT AAT ACC TCG CTC
Trp Leu Asn Met Thr Ile Gly Val Asn Thr Ser Leu
```

*FIG. 1B*

```
       950           960              970            980
AAC TTC GTC ACC AGT CCG CTG CAT ATA TTC AGC GTG
Asn Phe Val Thr Ser Pro Leu His Ile Phe Ser Val
         990           1000             1010
ACA GCC CTG GAC TCG CTC CCG AAC ACC CAC ACG GTG
Thr Ala Leu Asp Ser Leu Pro Asn Thr His Thr Val
  1020          1030            1040          1050
    ACT ATG ATG GTG CAA GTG GCG AAT GTG AAC AGC
    Thr Met Met Val Gln Val Ala Asn Val Asn Ser
          1060          1070           1080
CGT CCG CCG CGC TGG CTG GAG ATC TTC GCT GTC CAA
Arg Pro Pro Arg Trp Leu Glu Ile Phe Ala Val Gln
  1090           1100           1110          1120
    CAG TTT GAA GAG AAA TCT TAC CAA AAC TTC ACA
    Gln Phe Glu Glu Lys Ser Tyr Gln Asn Phe Thr
            1130          1140          1150
GTG AGG GCG ATC GAC GGA GAC ACT GAG ATC AAT ATG
Val Arg Ala Ile Asp Gly Asp Thr Glu Ile Asn Met
   1160          1170           1180          1190
CCT ATC AAC TAC AGG CTG ATC ACA AAT GAG GAA GAC
Pro Ile Asn Tyr Arg Leu Ile Thr Asn Glu Glu Asp
         1200           1210          1220
ACA TTC TTC AGC ATT GAG GCC CTG CCT GGT GGA AAA
Thr Phe Phe Ser Ile Glu Ala Leu Pro Gly Gly Lys
  1230          1240            1250          1260
    AGC GGG GCT GTA TTC CTC GTG TCG CCA ATT GAC
    Ser Gly Ala Val Phe Leu Val Ser Pro Ile Asp
          1270          1280           1290
CGC GAC ACA CTG CAA CGA GAG GTG TTT CCA CTT ACG
Arg Asp Thr Leu Gln Arg Glu Val Phe Pro Leu Thr
 1300          1310            1320          1330
  ATC GTC GCT TAC AAA TAT GAT GAG GAG GCC TTC TCC
  Ile Val Ala Tyr Lys Tyr Asp Glu Glu Ala Phe Ser
          1340          1350          1360
ACA TCA ACA AAC GTG GTC ATC ATT GTG ACA GAC ATC
Thr Ser Thr Asn Val Val Ile Ile Val Thr Asp Ile
```

FIG. 1C

```
       1370            1380            1390            1400
    AAC GAC CAA AGA CCT GAA CCT ATA CAC AAG GAA
    Asn Asp Gln Arg Pro Glu Pro Ile His Lys Glu
         1410            1420            1430
TAT CGA CTG GCA ATC ATG GAG GAG ACG CCC CTG ACC
Tyr Arg Leu Ala Ile Met Glu Glu Thr Pro Leu Thr
1440            1450            1460            1470
    CTC AAC TTC GAT AAA GAA TTC GGA TTT CAT GAT
    Leu Asn Phe Asp Lys Glu Phe Gly Phe His Asp
          1480            1490            1500
AAG GAT TTA GGT CAA AAC GCT CAG TAC ACG GTG CGT
Lys Asp Leu Gly Gln Asn Ala Gln Tyr Thr Val Arg
1510            1520            1530            1540
   CTA GAG AGC GTG GAC CCT CCA GGC GCT GCT GAG GCA
   Leu Glu Ser Val Asp Pro Pro Gly Ala Ala Glu Ala
         1550            1560            1570
TTC TAC ATA GCG CCT GAA GTC GGC TAC CAG CGA CAG
Phe Tyr Ile Ala Pro Glu Val Gly Tyr Gln Arg Gln
1580            1590            1600            1610
    ACC TTC ATC ATG GGC ACC CTC AAT CAC TCC ATG
    Thr Phe Ile Met Gly Thr Leu Asn His Ser Met
         1620            1630            1640
CTG GAT TAC GAA GTG CCA GAG TTT CAG AGT ATT ACG
Leu Asp Tyr Glu Val Pro Glu Phe Gln Ser Ile Thr
1650            1660            1670            1680
    ATT CGG GTG GTA GCG ACC GAC AAC AAC GAC ACG
    Ile Arg Val Val Ala Thr Asp Asn Asn Asp Thr
          1690            1700            1710
AGG CAC GTG GGC GTC GCG TTG GTT CAC ATT GAC CTC
Arg His Val Gly Val Ala Leu Val His Ile Asp Leu
1720            1730            1740            1750
    ATC AAT TGG AAC GAT GAG CAG CCG ATC TTC GAA CAC
    Ile Asn Trp Asn Asp Glu Gln Pro Ile Phe Glu His
          1760            1770            1780
GCC GTG CAG ACC GTC ACC TTC GAC GAG ACT GAA GGC
Ala Val Gln Thr Val Thr Phe Asp Glu Thr Glu Gly
```

*FIG. 1D*

```
    1790        1800        1810        1820
   GAG GGG TTC TTC GTC GCC AAG GCG GTT GCA CAC
   Glu Gly Phe Phe Val Ala Lys Ala Val Ala His
       1830        1840        1850
GAC AGA GAC ATC GGG GAT GTC GTC GAG CAT ACT TTA
Asp Arg Asp Ile Gly Asp Val Val Glu His Thr Leu
1860        1870        1880        1890
   TTG GGT AAC GCT GTT AAC TTC CTG ACC ATC GAC
   Leu Gly Asn Ala Val Asn Phe Leu Thr Ile Asp
         1900        1910        1920
AAA CTC ACC GGC GAC ATC CGC GTC TCA GCT AAC GAC
Lys Leu Thr Gly Asp Ile Arg Val Ser Ala Asn Asp
1930        1940        1950        1960
 TCC TTC AAC TAC CAT CGA GAA AGT GAA TTA TTT GTG
 Ser Phe Asn Tyr His Arg Glu Ser Glu Leu Phe Val
       1970        1980        1990
CAG GTG CGA GCT ACA GAC ACG CTG GGC GAA CCC TTC
Gln Val Arg Ala Thr Asp Thr Leu Gly Glu Pro Phe
2000        2010        2020        2030
    CAC ACG GCG ACG TCA CAG CTG GTC ATA CGA CTA
    His Thr Ala Thr Ser Gln Leu Val Ile Arg Leu
       2040        2050        2060
AAT GAC ATC AAC AAC ACG CCA CCC ACC TTA CGG CTG
Asn Asp Ile Asn Asn Thr Pro Pro Thr Leu Arg Leu
2070        2080        2090        2100
   CCT CGA GGC AGT CCC CAA GTG GAG GAG AAC GTG
   Pro Arg Gly Ser Pro Gln Val Glu Glu Asn Val
       2110        2120        2130
CCT GAT GGC CAC GTC ATC ACC CAG GAG TTA CGC GCC
Pro Asp Gly His Val Ile Thr Gln Glu Leu Arg Ala
2140        2150        2160        2170
 ACC GAC CCC GAC ACC ACG GCC GAT CTG CGC TTC GAG
 Thr Asp Pro Asp Thr Thr Ala Asp Leu Arg Phe Glu
       2180        2190        2200
ATA AAC TGG GAC ACC TCT TTC GCC ACC AAG CAA GGC
Ile Asn Trp Asp Thr Ser Phe Ala Thr Lys Gln Gly
```

*FIG. 1E*

```
         2210              2220             2230              2240
     CGC CAG GCT AAC CCC GAC GAG TTT AGG AAT TGC
     Arg Gln Ala Asn Pro Asp Glu Phe Arg Asn Cys
         2250              2260             2270
GTG GAA ATC GAG ACC ATC TTC CCC GAG ATT AAC AAC
Val Glu Ile Glu Thr Ile Phe Pro Glu Ile Asn Asn
   2280              2290             2300              2310
   CGG GGA CTG GCT ATC GGC CGC GTT GTA GCG CGC
   Arg Gly Leu Ala Ile Gly Arg Val Val Ala Arg
             2320              2330             2340
     GAA ATC AGA CAC AAC GTG ACC ATA GAC TAC GAG GAG
     Glu Ile Arg His Asn Val Thr Ile Asp Tyr Glu Glu
     2350              2360             2370              2380
     TTT GAG GTC CTC TCC CTC ACA GTG AGG GTG CGT GAC
     Phe Glu Val Leu Ser Leu Thr Val Arg Val Arg Asp
             2390              2400             2410
CTT AAC ACC GTC TAC GGA GAC GAC TAC GAC GAA TCG
Leu Asn Thr Val Tyr Gly Asp Asp Tyr Asp Glu Ser
   2420              2430             2440              2450
     ATG CTC ACA ATA ACT ATA ATC GAT ATG AAC GAC
     Met Leu Thr Ile Thr Ile Ile Asp Met Asn Asp
             2460              2470             2480
AAC GCG CCG GTG TGG GTG GAG GGG ACT CTG GAG CAG
Asn Ala Pro Val Trp Val Glu Gly Thr Leu Glu Gln
   2490              2500             2510              2520
     AAC TTC CGA GTC CGC GAG ATG TCG GCG GGC GGG
     Asn Phe Arg Val Arg Glu Met Ser Ala Gly Gly
             2530              2540             2550
CTC GTG GTG GGC TCC GTG CGC GCG GAC GAC ATC GAC
Leu Val Val Gly Ser Val Arg Ala Asp Asp Ile Asp
2560              2570             2580              2590
   GGA CCG CTC TAC AAC CAA GTG CGA TAC ACC ATT TTC
   Gly Pro Leu Tyr Asn Gln Val Arg Tyr Thr Ile Phe
             2600              2610             2620
CCT CGT GAA GAC ACA GAT AAG GAC CTG ATA ATG ATC
Pro Arg Glu Asp Thr Asp Lys Asp Leu Ile Met Ile
```

*FIG. 1F*

```
             2630           2640            2650           2660
      GAC TTC CTC ACG GGT CAA ATT TCC GTG AAC ACA
      Asp Phe Leu Thr Gly Gln Ile Ser Val Asn Thr
         2670           2680           2690
AGC GGC GCC ATC GAC GCG GAT ACT CCT CCA CGC TTC
Ser Gly Ala Ile Asp Ala Asp Thr Pro Pro Arg Phe
2700           2710           2720           2730
     CAC CTC TAC TAT ACA GTG GTC GCT AGT GAC CGA
     His Leu Tyr Tyr Thr Val Val Ala Ser Asp Arg
         2740           2750           2760
TGC TCG ACA GAA GAT CCT GCA GAT TGC CCC CCT GAC
Cys Ser Thr Glu Asp Pro Ala Asp Cys Pro Pro Asp
2770           2780           2790           2800
  CCG ACT TAT TGG GAA ACC GAA GGA AAT ATC ACA ATC
  Pro Thr Tyr Trp Glu Thr Glu Gly Asn Ile Thr Ile
        2810           2820           2830
CAC ATC ACC GAC ACG AAC AAC AAG GTC CCG CAG GCG
His Ile Thr Asp Thr Asn Asn Lys Val Pro Gln Ala
2840           2850           2860           2870
     GAA ACG ACT AAG TTC GAT ACC GTC GTG TAT ATT
     Glu Thr Thr Lys Phe Asp Thr Val Val Tyr Ile
         2880           2890           2900
TAC GAG AAC GCA ACC CAC TTA GAC GAG GTG GTC.ACT
Tyr Glu Asn Ala Thr His Leu Asp Glu Val Val Thr
2910           2920           2930           2940
   CTG ATA GCC AGT GAT CTT GAC AGA GAC GAA ATA
   Leu Ile Ala Ser Asp Leu Asp Arg Asp Glu Ile
         2950           2960           2970
TAC CAC ACG GTG AGC TAC GTC ATC AAT TAT GCA GTG
Tyr His Thr Val Ser Tyr Val Ile Asn Tyr Ala Val
2980           2990           3000           3010
  AAC CCT CGA CTG ATG AAC TTC TTC TCC GTG AAC CGA
  Asn Pro Arg Leu Met Asn Phe Phe Ser Val Asn Arg
        3020           3030           3040
GAG ACC GGC CTG GTG TAC GTG GAC TAT GAG ACC CAG
Glu Thr Gly Leu Val Tyr Val Asp Tyr Glu Thr Gln
```

*FIG. 1G*

```
     3050         3060         3070         3080
    GGT AGT GGC GAG GTG CTG GAC CGT GAT GGT GAT
    Gly Ser Gly Glu Val Leu Asp Arg Asp Gly Asp
        3090         3100         3110
GAA CCA ACG CAC CGT ATC TTC TTC AAC CTC ATC GAC
Glu Pro Thr His Arg Ile Phe Phe Asn Leu Ile Asp
3120         3130         3140         3150
    AAC TTC ATG GGG GAA GGA GAA GGT AAC AGA AAT
    Asn Phe Met Gly Glu Gly Glu Gly Asn Arg Asn
         3160         3170         3180
CAG AAC GAC ACA GAA GTT CTC GTT ATC TTG TTG GAT
Gln Asn Asp Thr Glu Val Leu Val Ile Leu Leu Asp
3190         3200         3210         3220
   GTG AAT GAC AAT GCT CCT GAA TTG CCA CCG AGC
   Val Asn Asp Asn Ala Pro Glu Leu Pro Pro Ser
        3230         3240         3250
GAA CTC TCT TGG ACT ATA TCT GAG AAC CTT AAG CAG
Glu Leu Ser Trp Thr Ile Ser Glu Asn Leu Lys Gln
3260         3270         3280         3290
    GGC GTC CGT CTT GAA CCA CAT ATC TTC GCC CCG
    Gly Val Arg Leu Glu Pro His Ile Phe Ala Pro
         3300         3310         3320
GAC CGC GAC GAG CCC GAC ACA GAC AAC TCC AGG GTC
Asp Arg Asp Glu Pro Asp Thr Asp Asn Ser Arg Val
3330         3340         3350         3360
    GGC TAC GAG ATC CTG AAC CTC AGC ACG GAG CGG
    Gly Tyr Glu Ile Leu Asn Leu Ser Thr Glu Arg
         3370         3380         3390
GAC ATC GAA GTG CCG GAG CTG TTT GTG ATG ATA CAG
Asp Ile Glu Val Pro Glu Leu Phe Val Met Ile Gln
3400         3410         3420         3430
    ATC GCG AAC GTC ACG GGA GAG CTG GAG ACC GCC ATG
    Ile Ala Asn Val Thr Gly Glu Leu Glu Thr Ala Met
         3440         3450         3460
GAC CTC AAG GGA TAT TGG GGG ACG TAC GCT ATA CAT
Asp Leu Lys Gly Tyr Trp Gly Thr Tyr Ala Ile His
```

FIG. 1H

```
         3470           3480           3490           3500
      ATA CGG GCA TTC GAC CAC GGC ATT CCG CAA ATG
      Ile Arg Ala Phe Asp His Gly Ile Pro Gln Met
            3510           3520           3530
   TCC ATG AAC GAG ACA TAT GAG CTG ATC ATC CAT CCG
   Ser Met Asn Glu Thr Tyr Glu Leu Ile Ile His Pro
   3540           3550           3560           3570
      TTC AAC TAC TAC GCG CCT GAG TTC GTC TTC CCG
      Phe Asn Tyr Tyr Ala Pro Glu Phe Val Phe Pro
            3580           3590           3600
   ACC AAC GAT GCC GTC ATA CGA CTT GCG AGG GAA CGA
   Thr Asn Asp Ala Val Ile Arg Leu Ala Arg Glu Arg
   3610           3620           3630           3640
     GCT GTA ATC AAT GGA GTT CTA GCG ACA GTG AAC GGA
     Ala Val Ile Asn Gly Val Leu Ala Thr Val Asn Gly
            3650           3660           3670
   GAG TTC TTG GAG CGG ATA TCG GCG ACT GAT CCG GAC
   Glu Phe Leu Glu Arg Ile Ser Ala Thr Asp Pro Asp
   3680           3690           3700           3710
      GGA CTC CAC GCG GGC GTC GTC ACC TTC CAA GTG
      Gly Leu His Ala Gly Val Val Thr Phe Gln Val
            3720           3730           3740
   GTA GGC GAT GAG GAA TCA CAA CGG TAC TTT CAA GTA
   Val Gly Asp Glu Glu Ser Gln Arg Tyr Phe Gln Val
   3750           3760           3770           3780
      GTT AAC GAT GGC GAG AAC CTC GGC TCG TTG AGG
      Val Asn Asp Gly Glu Asn Leu Gly Ser Leu Arg
            3790           3800           3810
   TTA CTG CAA GCC GTT CCA GAG GAG ATC AGG GAG TTC
   Leu Leu Gln Ala Val Pro Glu Glu Ile Arg Glu Phe
   3820           3830           3840           3850
     CGG ATA ACG ATT CGC GCT ACA GAC CAG GGA ACG GAC
     Arg Ile Thr Ile Arg Ala Thr Asp Gln Gly Thr Asp
            3860           3870           3880
   CCA GGA CCG CTG TCC ACG GAC ATG ACG TTC AGA GTT
   Pro Gly Pro Leu Ser Thr Asp Met Thr Phe Arg Val
```

*FIG. 1I*

```
     3890          3900          3910          3920
    GTT TTT GTG CCC ACG CAA GGA GAA CCT AGA TTC
    Val Phe Val Pro Thr Gln Gly Glu Pro Arg Phe
       3930          3940          3950
GCG TCC TCA GAA CAT GCT GTC GCT TTC ATA GAA AAG
Ala Ser Ser Glu His Ala Val Ala Phe Ile Glu Lys
   3960          3970          3980          3990
   AGT GCC GGC ATG GAA GAG TCT CAC CAA CTT CCT
   Ser Ala Gly Met Glu Glu Ser His Gln Leu Pro
         4000          4010          4020
CTA GCA CAA GAC ATC AAG AAC CAT CTC TGT GAA GAC
Leu Ala Gln Asp Ile Lys Asn His Leu Cys Glu Asp
   4030          4040          4050          4060
   GAC TGT CAC AGC ATT TAC TAT CGT ATT ATC GAT GGC
   Asp Cys His Ser Ile Tyr Tyr Arg Ile Ile Asp Gly
         4070          4080          4090
AAC AGC GAA GGT CAT TTC GGC CTG GAT CCT GTT CGC
Asn Ser Glu Gly His Phe Gly Leu Asp Pro Val Arg
   4100          4110          4120          4130
      AAC AGG TTG TTC CTG AAG AAA GAG CTG ATA AGG
      Asn Arg Leu Phe Leu Lys Lys Glu Leu Ile Arg
         4140          4150          4160
GAA CAA AGT GCC TCC CAC ACT CTG CAA GTG GCG, GCT
Glu Gln Ser Ala Ser His Thr Leu Gln Val Ala Ala
   4170          4180          4190          4200
     AGT AAC TCG CCC GAT GGT GGC ATT CCA CTT CCT
     Ser Asn Ser Pro Asp Gly Gly Ile Pro Leu Pro
            4210          4220          4230
GCT TCC ATC CTT ACT GTC ACT GTT ACC GTG AGG GAG
Ala Ser Ile Leu Thr Val Thr Val Thr Val Arg Glu
   4240          4250          4260          4270
     GCA GAC CCT CGT CCA GTG TTT GTG AGG GAA TTG TAC
     Ala Asp Pro Arg Pro Val Phe Val Arg Glu Leu Tyr
            4280          4290          4300
ACC GCA GGG ATA TCC ACA GCG GAC TCC ATC GGC AGA
Thr Ala Gly Ile Ser Thr Ala Asp Ser Ile Gly Arg
```

*FIG. 1J*

```
       4310           4320           4330              4340
        GAG CTG CTC AGA TTA CAT GCG ACC CAG TCT GAA
        Glu Leu Leu Arg Leu His Ala Thr Gln Ser Glu
           4350           4360           4370
    GGC TCG GCC ATT ACT TAT GCT ATA GAC TAC GAT ACA
    Gly Ser Ala Ile Thr Tyr Ala Ile Asp Tyr Asp Thr
    4380           4390           4400           4410
       ATG GTA GTG GAC CCC AGC CTG GAG GCA GTG AGA
       Met Val Val Asp Pro Ser Leu Glu Ala Val Arg
          4420           4430           4440
    CAG TCG GCT TTC GTA CTG AAC GCT CAA ACC GGA GTG
    Gln Ser Ala Phe Val Leu Asn Ala Gln Thr Gly Val
    4450           4460           4470           4480
       CTG ACG CTT AAT ATC AGC CCA CGG CCA CGA TGC AT
       Leu Thr Leu Asn Ile Gln Pro Thr Ala Thr Met His
          4490           4500           4510
    GGA CTG TTC AAA TTC GAA GTC ACA GCT ACT GAC ACG
    Gly Leu Phe Lys Phe Glu Val Thr Ala Thr Asp Thr
    4520           4530           4540           4550
        GCC GGC GCT CAG GAC CGC ACC GAC GTC ACC GTG
        Ala Gly Ala Gln Asp Arg Thr Asp Val Thr Val
           4560           4570           4580
    TAC GTG GTA TCC TCG CAG AAC CGC GTC TAC TTC GTG
    Tyr Val Val Ser Ser Gln Asn Arg Val Tyr Phe Val
    4590           4600           4610           4620
       TTC GTC AAC ACG CTG CAA CAG GTC GAA GAC AAC
       Phe Val Asn Thr Leu Gln Gln Val Glu Asp Asn
          4630           4640           4650
    AGA GAC TTT ATC GCG GAC ACC TTC AGC GCT GGG TTC
    Arg Asp Phe Ile Ala Asp Thr Phe Ser Ala Gly Phe
    4660           4670           4680           4690
     AAC ATG ACC TGC AAC ATC GAC CAA GTG GTG CCC GCT
     Asn Met Thr Cys Asn Ile Asp Gln Val Val Pro Ala
          4700           4710           4720
    AAC GAC CCC GTC ACC GGC GTG GCG CTG GAG CAC AGC
    Asn Asp Pro Val Thr Gly Val Ala Leu Glu His Ser
```

*FIG. 1K*

```
     4730           4740          4750           4760
   ACG CAG ATG CGC GGC CAC TTC ATA CGG GAC AAC
   Thr Gln Met Arg Gly His Phe Ile Arg Asp Asn
        4770          4780          4790
GTA CCC GTA CTC GCT GAT GAG ATA GAA CAG ATC CGT
Val Pro Val Leu Ala Asp Glu Ile Glu Gln Ile Arg
   4800          4810          4820          4830
   AGT GAC CTA GTC CTC CTG AGC TCG ATA CAA ACA
   Ser Asp Leu Val Leu Leu Ser Ser Ile Gln Thr
         4840          4850          4860
ACG CTG GCG GCG CGA TCG CTG GTG TTG CAG GAC TTG
Thr Leu Ala Ala Arg Ser Leu Val Leu Gln Asp Leu
    4870          4880          4890          4900
   TTG ACC AAC TCC AGC CCG GAC TCG GCG CCT GAC TCG
   Leu Thr Asn Ser Ser Pro Asp Ser Ala Pro Asp Ser
         4910          4920          4930
AGC CTC ACG GTG TAC GTG CTG GCC TCA CTG TCT GCT
Ser Leu Thr Val Try Val Leu Ala Ser Leu Ser Ala
    4940          4950          4960          4970
     GTG CTC GGT TTC ATG TGC CTT GTG CTA CTG CTT
     Val Leu Gly Phe Met Cys Leu Val Leu Leu Leu
          4980          4990          5000
ACC TTC ATC ATC AGG ACT AGA GCG CTA AAC CGA CGG
Thr Phe Ile Ile Arg Thr Arg Ala Leu Asn Arg Arg
   5010          5020          5030          5040
    TTG GAA GCC CTG TCG ATG ACG AAG TAC GGC TCA
    Leu Glu Ala Leu Ser Met Thr Lys Tyr Gly Ser
          5050          5060          5070
CTG GAC TCT GGA TTG AAC CGC GCC GGC ATC GCC GCC
Leu Asp Ser Gly Leu Asn Arg Ala Gly Ile Ala Ala
   5080          5090          5100          5110
   CCC GGC ACC AAC AAA CAC ACT GTG AAA GGC TCC AAC
   Pro Gly Thr Asn Lys His Thr Val Glu Gly Ser Asn
         5120          5130          5140
CCT ATC TTC AAT GAA GCA ATA AAG ACG CCA GAT TTA
Pro Ile Phe Asn Glu Ala Ile Lys Thr Pro Asp Leu
```

*FIG. 1L*

```
             5150                5160                5170                5180
       GAT GCC ATT AGC GAG GGT TCC AAC GAC TCT GAT
       Asp Ala Ile Ser Glu Gly Ser Asn Asp Ser Asp
           5190                5200                5210
CTG ATC GGC ATC GAA GAT CTT CCG CAC TTT GGC AAC
Leu Ile Gly Ile Glu Asp Leu Pro His Phe Gly Asn
5220                5230                5240                5250
    GTC TTC ATG GAT CCT GAG GTG AAC GAA AAG GCA
    Val Phe Met Asp Pro Glu Val Asn Glu Lys Ala
         5260                5270                5280
AAT GGT TAT CCC GAA GTC GCA AAC CAC AAC AAC AAC
Asn Gly Tyr Pro Glu Val Ala Asn His Asn Asn Asn
5290                5300                5310                5320
  TTC GCT TTC AAC CCG ACT CCC TTC TCG CCT GAG TTC
  Phe Ala Phe Asn Pro Thr Pro Phe Ser Pro Glu Phe
        5330                5340                5350                5360
   GTT AAC GGA CAG TTC AGA AAG ATC TAGAAGATAACAACA
   Val Asn Gly Gln Phe Arg Lys Ile
         5370               5380               5390        5400          5410
CTAGTTAAGATCATTAATTTTGGAGTTTGGAATTAAGATTTTTGAAAG
         5420          5430           5440               5450
GATAGTTGTGATAAGCCTGTGATTTTTAAAACTGTAATTGAAAAAA
5460         5470          5480         5490         5500
AAAATTGAGACCTCCATTTAAGCTCTTGCTCTCATCTCATCAAATTTT
    5510         5520         5530         5540         5550
ATAAAATGCCATTAGTCATTAAGATACTCGATTTAATTTAAGATTATT
       5560         5570         5580
TAAGATATTATGTAAAATAAATATATTGTC
```

FIG. 1M

SEQ ID NO.2

| | | | | | | | | | |
|---|---|---|---|---|---|---|---|---|---|
| Met 1 | Ala | Val | Asp | Val 5 | Arg | Ile | Ala | Ala | Phe 10 | Leu | Leu |
| Val | Phe | Ile 15 | Ala | Pro | Ala | Val | Leu 20 | Ala | Gln | Glu | Arg |
| Cys 25 | Gly | Tyr | Met | Thr 30 | Ala | Ile | Pro | Arg | Leu 35 | Pro | Arg |
| Pro | Asp | Asn | Leu 40 | Pro | Val | Leu | Asn | Phe 45 | Glu | Gly | Gln |
| Thr | Trp 50 | Ser | Gln | Arg | Pro | Leu 55 | Leu | Pro | Ala | Pro | Glu 60 |

|CAD1

| Arg | Asp | Asp | Leu | Cys 65 | Met | Asp | Ala | Tyr | His 70 | Val | Ile |
| Thr | Ala | Asn 75 | Leu | Gly | Thr | Gln | Val | Ile 80 | Tyr | Met | Asp |
| Glu 85 | Glu | Ile | Glu | Asp | Glu 90 | Ile | Thr | Ile | Ala | Ile 95 | Leu |
| Asn | Tyr | Asn | Gly 100 | Pro | Ser | Thr | Pro | Phe 105 | Ile | Glu | Leu |
| Pro | Phe 110 | Leu | Ser | Gly | Ser | Tyr 115 | Asn | Leu | Leu | Met | Pro 120 |
| Val | Ile | Arg | Arg | Val 125 | Asp | Asn | Gly | Glu | Trp 130 | His | Leu |
| Ile | Ile | Thr 135 | Gln | Arg | Gln | His | Tyr 140 | Glu | Leu | Pro | Gly |
| Met 145 | Gln | Gln | Tyr | Met | Phe 150 | Asn | Val | Arg | Val | Asp 155 | Gly |
| Gln | Ser | Leu | Val 160 | Ala | Gly | Val | Ser | Leu 165 | Ala | Ile | Val |

CAD2→

| Asn | Ile | Asp 170 | Asp | Asn | Ala | Pro 175 | Ile | Ile | Gln | Asn | Phe 180 |
| Glu | Pro | Cys | Arg | Val 185 | Pro | Glu | Leu | Gly | Glu 190 | Pro | Gly |
| Leu | Thr | Glu 195 | Cys | Thr | Tyr | Gln | Val 200 | Ser | Asp | Ala | Asp |
| Gly 205 | Arg | Ile | Ser | Thr | Glu 210 | Phe | Met | Thr | Phr | Arg 215 | Ile |

FIG. 2A

Asp Ser Val Arg Gly Asp Glu Glu Thr Phe Tyr Ile
            220                    225
Glu Arg Thr Asn Ile Pro Asn Gln Trp Met Trp Leu
        230              235                240
Asn Met Thr Ile Gly Val Asn Thr Ser Leu Asn Phe
                245              250
Val Thr Ser Pro Leu His Ile Phe Ser Val Thr Ala
        255              260
Leu Asp Ser Leu Pro Asn Thr His Thr Val Thr Met
265              270              275
Met Val Gln Val Ala Asn Val Asn Ser Arg Pro Pro
            280                    285
    ⌐CAD3⎯⎯→
Arg Trp Leu Glu Ile Phe Ala Val Gln Gln Phe Glu
    290              295                    300
Glu Lys Ser Tyr Gln Asn Phe Thr Val Arg Ala Ile
                305              310
Asp Gly Asp Thr Glu Ile Asn Met Pro Ile Asn Tyr
        315              320
Arg Leu Ile Thr Asn Glu Glu Asp Thr Phe Phe Ser
325              330              335
Ile Glu Ala Leu Pro Gly Gly Lys Ser Gly Ala Val
            340              345
Phe Leu Val Ser Pro Ile Asp Arg Asp Thr Leu·Gln
    350              355              360
Arg Glu Val Phe Pro Leu Thr Ile Val Ala Tyr Lys
                365              370
Tyr Asp Glu Glu Ala Phe Ser Thr Ser Thr Asn Val
        375              380
Val Ile Ile Val Thr Asp Ile Asn Asp Gln Arg Pro
385     ⌐CAD4⎯⎯→   390              395
Glu Pro Ile His Lys Glu Tyr Arg Leu Ala Ile Met
            400              405
Glu Glu Thr Pro Leu Thr Leu Asn Phe Asp Lys Glu
    410              415                    420
Phe Gly Phe His Asp Lys Asp Leu Gly Gln Asn Ala
            425              430

*FIG. 2B*

```
     Gln Tyr Thr Val Arg Leu Glu Ser Val Asp Pro Pro
             435                 440
     Gly Ala Ala Glu Ala Phe Tyr Ile Ala Pro Glu Val
     445                 450                 455
     Gly Tyr Gln Arg Gln Thr Phe Ile Met Gly Thr Leu
                 460                 465
     Asn His Ser Met Leu Asp Tyr Glu Val Pro Glu Phe
         470                 475                 480
     Gln Ser Ile Thr Ile Arg Val Val Ala Thr Asp Asn
                     485         CAD5    490
     Asn Asp Thr Arg His Val Gly Val Ala Leu Val His
             495                 500
     Ile Asp Leu Ile Asn Trp Asn Asp Glu Gln Pro Ile
     505                 510                 515
     Phe Glu His Ala Val Gln Thr Val Thr Phe Asp Glu
                 520                 525
     Thr Glu Gly Glu Gly Phe Phe Val Ala Lys Ala Val
         530                 535                 540
     Ala His Asp Arg Asp Ile Gly Asp Val Val Glu His
                     545                 550
     Thr Leu Leu Gly Asn Ala Val Asn Phe Leu Thr Ile
             555                 560
     Asp Lys Leu Thr Gly Asp Ile Arg Val Ser Ala Asn
     565                 570                 575
     Asp Ser Phe Asn Tyr His Arg Glu Ser Glu Leu Phe
                 580                 585
     Val Gln Val Arg Ala Thr Asp Thr Leu Gly Glu Pro
         590                 595                 600
     Phe His Thr Ala Thr Ser Gln Leu Val Ile Arg Leu
                     605                 610    CAD6
     Asn Asp Ile Asn Asn Thr Pro Pro Thr Leu Arg Leu
     →       615                 620
     Pro Arg Gly Ser Pro Gln Val Glu Glu Asn Val Pro
     625                 630                 635
     Asp Gly His Val Ile Thr Gln Glu Leu Arg Ala Thr
                 640                 645
```

*FIG. 2C*

```
Asp Pro Asp Thr Thr Ala Asp Leu Arg Phe Glu Ile
        650                 655                 660
Asn Trp Asp Thr Ser Phe Ala Thr Lys Gln Gly Arg
                665                 670
Gln Ala Asn Pro Asp Glu Phe Arg Asn Cys Val Glu
        675                 680
Ile Glu Thr Ile Phe Pro Glu Ile Asn Asn Arg Gly
685                 690                 695
Leu Ala Ile Gly Arg Val Val Ala Arg Glu Ile Arg
                700                 705
His Asn Val Thr Ile Asp Tyr Glu Glu Phe Glu Val
        710                 715                 720
Leu Ser Leu Thr Val Arg Val Arg Asp Leu Asn Thr
                725                 730
Val Tyr Gly Asp Asp Tyr Asp Glu Ser Met Leu Thr
        735                 740
Ile Thr Ile Ile Asp Met Asn Asp Asn Ala Pro Val
745                 750                 755 CAD7
Trp Val Glu Gly Thr Leu Glu Gln Asn Phe Arg Val
⟶               760                 765
Arg Glu Met Ser Ala Gly Gly Leu Val Val Gly Ser
        770                 775                 780
Val Arg Ala Asp Asp Ile Asp Gly Pro Leu Tyr·Asn
                785                 790
Gln Val Arg Tyr Thr Ile Phe Pro Arg Glu Asp Thr
        795                 800
Asp Lys Asp Leu Ile Met Ile Asp Phe Leu Thr Gly
805                 810                 815
Gln Ile Ser Val Asn Thr Ser Gly Ala Ile Asp Ala
                820                 825
Asp Thr Pro Pro Arg Phe His Leu Tyr Tyr Thr Val
        830                 835                 840
Val Ala Ser Asp Arg Cys Ser Thr Glu Asp Pro Ala
                845                 850
Asp Cys Pro Pro Asp Pro Thr Tyr Trp Glu Thr Glu
        855                 860
```

*FIG. 2D*

```
Gly Asn Ile Thr Ile His Ile Thr Asp Thr Asn Asn
865                     870                 875
                            ┌CAD8──────▶
Lys Val Pro Gln Ala Glu Thr Thr Lys Phe Asp Thr
            880             885
Val Val Tyr Ile Tyr Glu Asn Ala Thr His Leu Asp
        890             895             900
Glu Val Val Thr Leu Ile Ala Ser Asp Leu Asp Arg
                905             910
Asp Glu Ile Tyr His Thr Val Ser Tyr Val Ile Asn
        915                 920
Tyr Ala Val Asn Pro Arg Leu Met Asn Phe Phe Ser
925             930                     935
Val Asn Arg Glu Thr Gly Leu Val Tyr Val Asp Tyr
            940                 945
Glu Thr Gln Gly Ser Gly Glu Val Leu Asp Arg Asp
    950                 955                 960
Gly Asp Glu Pro Thr His Arg Ile Phe Phe Asn Leu
                965                 970
Ile Asp Asn Phe Met Gly Glu Gly Glu Gly Asn Arg
        975                 980
Asn Gln Asn Asp Thr Glu Val Leu Val Ile  Leu Leu
985                 990                     995
                                       ┌CAD9──▶
Asp Val Asn Asp Asn Ala Pro Glu Leu Pro Pro Pro
            1000                1005
Ser Glu Leu Ser Trp Thr Ile Ser Glu Asn Leu Lys
    1010                1015                1020
Gln Gly Val Arg Leu Glu Pro His Ile Phe Ala Pro
                1025                1030
Asp Arg Asp Glu Pro Asp Thr Asp Asn Ser Arg Val
        1035                1040
Gly Tyr Glu Ile Leu Asn Leu Ser Thr Glu Arg Asp
1045                1050                1055
Ile Glu Val Pro Glu Leu Phe Val Met Ile Gln Ile
                1060                1065
Ala Asn Val Thr Gly Glu Leu Glu Thr Ala Met Asp
    1070                1075                1080
```

*FIG. 2E*

```
Leu Lys Gly Tyr Trp Gly Thr Tyr Ala Ile His Ile
              1085                1090
Arg Ala Phe Asp His Gly Ile Pro Gln Met Ser Met
          1095                1100
Asn Glu Thr Tyr Glu Leu Ile Ile His Pro Phe Asn
1105                1110 CAD10        1115
Tyr Tyr Ala Pro Glu Phe  Val Phe Pro Thr Asn Asp
              1120           1125
Ala Val Ile Arg Leu Ala Arg Glu Arg Ala Val Ile
          1130         1135             1140
Asn Gly Val Leu Ala Thr Val Asn Gly Glu Phe Leu
              1145               1150
Glu Arg Ile Ser Ala Thr Asp Pro Asp Gly Leu His
          1155               1160
Ala Gly Val Val Thr Phe Gln Val Val Gly Asp Glu
1165                1170             1175
Glu Ser Gln Arg Tyr Phe Gln Val Val Asn Asp Gly
              1180               1185
Glu Asn Leu Gly Ser Leu Arg Leu Leu Gln Ala Val
          1190         1195             1200
Pro Glu Glu Ile Arg Glu Phe Arg Ile Thr Ile Arg
              1205               1210
Ala Thr Asp Gln Gly Thr Asp Pro Gly Pro Leu Ser
          1215               1220
Thr Asp Met Thr Phe Arg Val Val Phe Val Pro Thr
1225                1230 CAD11        1235
Gln Gly Glu Pro Arg Phe  Ala Ser Ser Glu His Ala
              1240               1245
Val Ala Phe Ile Glu Lys Ser Ala Gly Met Glu Glu
          1250         1255             1260
Ser His Gln Leu Pro Leu Ala Gln Asp Ile Lys Asn
              1265               1270
His Leu Cys Glu Asp Asp Cys His Ser Ile Tyr Tyr
              1275               1280
Arg Ile Ile Asp Gly Asn Ser Glu Gly His Phe Gly
1285                1290             1295
```

*FIG. 2F*

```
Leu Asp Pro Val Arg Asn Arg Leu Phe Leu Lys Lys
              1300                1305
Glu Leu Ile Arg Glu Gln Ser Ala Ser His Thr Leu
        1310            1315                1320
Gln Val Ala Ala Ser Asn Ser Pro Asp Gly Gly Ile
                1325            1330
Pro Leu Pro Ala Ser Ile Leu Thr Val Thr Val Thr
        1335                1340
Val Arg Glu Ala Asp Pro Arg Pro Val Phe Val Arg
1345                1350                1355
Glu Leu Tyr Thr Ala Gly Ile Ser Thr Ala Asp Ser
            1360                1365
Ile Gly Arg Glu Leu Leu Arg Leu His Ala Thr Gln
        1370            1375                1380
Ser Glu Gly Ser Ala Ile Thr Tyr Ala Ile Asp Tyr
                1385            1390
Asp Thr Met Val Val Asp Pro Ser Leu Glu Ala Val
            1395            1400
Arg Gln Ser Ala Phe Val Leu Asn Ala Gln Thr Gly
1405                1410                1415
Val Leu Thr Leu Asn Ile Gln Pro Thr Ala Thr Met
            1420                1425
His Gly Leu Phe Lys Phe Glu Val Thr Ala Thr Asp
        1430                1435                1440
Thr Ala Gly Ala Gln Asp Arg Thr Asp Val Thr Val
                1445                1450
Tyr Val Val Ser Ser Gln Asn Arg Val Tyr Phe Val
            1455                1460
Phe Val Asn Thr Leu Gln Gln Val Glu Asp Asn Arg
1465                1470                1475
Asp Phe Ile Ala Asp Thr Phe Ser Ala Gly Phe Asn
            1480                1485
Met Thr Cys Asn Ile Asp Gln Val Val Pro Ala Asn
        1490                1495                1500
Asp Pro Val Thr Gly Val Ala Leu Glu His Ser Thr
                1505                1510
```

FIG. 2G

Gln Met Arg Gly His Phe Ile Arg Asp Asn Val Pro
        1515                    1520
Val Leu Ala Asp Glu Ile Glu Gln Ile Arg Ser Asp
1525                1530                1535
Leu Val Leu Leu Ser Ler Ile Gln Thr Thr Leu Ala
            1540                1545
Ala Arg Ser Leu Val Leu Gln Asp Leu Leu Thr Asn
        1550                1555            1560
Ser Ser Pro Asp Ser Ala Pro Asp Ser Ser Leu Thr
                1565                1570
Val Thr Val Leu Ala Ser Leu Ser Ala Val Leu Gly
            1575                1580
Phe Met Cys Leu Val Leu Leu Leu Thr Phe Ile Ile
1585                1590                1595
Arg Thr Arg Ala Leu Asn Arg Arg Leu Glu Ala Leu
            1600                1605
Ser Met Thr Lys Tyr Gly Ser Leu Asp Ser Gly Leu
    1610                1615                1620
Asn Arg Ala Gly Ile Ala Ala Pro Gly Thr Asn Lys
                1625                1630
His Thr Val Glu Gly Ser Asn Pro Ile Phe Asn Glu
            1635                1640
Ala Ile Lys Thr Pro Asp Leu Asp Ala Ile Ser Glu
1645                1650                1655
Gly Ser Asn Asp Ser Asp Leu Ile Gly Ile Glu Asp
                1660                1665
Leu Pro His Phe Gly Asn Val Phe Met Asp Pro Glu
    1670                1675                1680
Val Asn Glu Lys Ala Asn Gly Tyr Pro Glu Val Ala
                1685                1690
Asn His Asn Asn Asn Phe Ala Phe Asn Pro Thr Pro
            1695                1700
Phe Ser Pro Glu Phe Val Asn Gly Gln Phe Arg Lys
1705                1710                1715
Ile

SEQUENCE LISTING

<160> NUMBER OF SEQ ID NOS: 15

<210> SEQ ID NO 1
<211> LENGTH: 5582
<212> TYPE: DNA
<213> ORGANISM: M. sexta
<220> FEATURE:
<221> NAME/KEY: CDS
<222> LOCATION: (197)...(5348)

<400> SEQUENCE: 1

```
gaccaatcgg agtgtggtga atttttggaa aatatttttgt gcggttcctt tagttgtgta      60
atatagtact ttagttacaa atttggaata atttggcagc aaaaccatct gcagcaacaa     120
aatcatctgc agctgcgaaa tcatctgcag cagcaaaagc atcttcagga gcgagaaaag     180
ccccaaataa tgtgag atg gca gtt gac gtc cga atc gct gcc ttc ctg ctg     232
              Met Ala Val Asp Val Arg Ile Ala Ala Phe Leu Leu
                1               5                  10 gtg ttt ata gcg cct gca gtt tta gct caa gag aga tgt ggg tat atg      280
Val Phe Ile Ala Pro Ala Val Leu Ala Gln Glu Arg Cys Gly Tyr Met
         15                  20                  25 acc gcc atc cca agg cta cca cga ccg gat aat ttg cca gta cta aat      328
Thr Ala Ile Pro Arg Leu Pro Arg Pro Asp Asn Leu Pro Val Leu Asn
     30                  35                  40 ttt gaa ggc cag aca tgg agt cag agg ccc ctg ctc ccc gcc ccg gag      376
```

-continued

```
            Phe Glu Gly Gln Thr Trp Ser Gln Arg Pro Leu Leu Pro Ala Pro Glu
             45                  50                  55                  60 cgg gat gac ctg tgc atg gac gcc tac cac gtg ata aca gcc aac ctc              424
Arg Asp Asp Leu Cys Met Asp Ala Tyr His Val Ile Thr Ala Asn Leu
                 65                  70                  75 ggc acg cag gtc atc tac atg gat gaa gag ata gaa gac gaa atc acc              472
Gly Thr Gln Val Ile Tyr Met Asp Glu Glu Ile Glu Asp Glu Ile Thr
             80                  85                  90 atc gcc ata ctt aat tat aac gga cca tca act ccg ttc att gaa ctg              520
Ile Ala Ile Leu Asn Tyr Asn Gly Pro Ser Thr Pro Phe Ile Glu Leu
         95                 100                 105 cca ttt tta tcc ggt tcg tac aat ctg ctg atg ccg gtc atc agg aga              568
Pro Phe Leu Ser Gly Ser Tyr Asn Leu Leu Met Pro Val Ile Arg Arg
    110                 115                 120 gtt gac aac ggg gag tgg cat ctc atc atc acg caa aga cag cat tac              616
Val Asp Asn Gly Glu Trp His Leu Ile Ile Thr Gln Arg Gln His Tyr
125                 130                 135                 140 gag ttg ccc ggc atg cag cag tac atg ttc aat gtg cgc gtg gac ggc              664
Glu Leu Pro Gly Met Gln Gln Tyr Met Phe Asn Val Arg Val Asp Gly
                145                 150                 155 cag tcg ctg gtg gca ggc gtg tct ctc gct atc gtc aac ata gat gac              712
Gln Ser Leu Val Ala Gly Val Ser Leu Ala Ile Val Asn Ile Asp Asp
            160                 165                 170 aac gcg ccc atc ata caa aac ttc gag cct tgc cgg gtt cct gaa ctg              760
Asn Ala Pro Ile Ile Gln Asn Phe Glu Pro Cys Arg Val Pro Glu Leu
        175                 180                 185 ggc gag cca ggg ttg aca gaa tgc aca tac caa gta tcg gac gcg gac              808
Gly Glu Pro Gly Leu Thr Glu Cys Thr Tyr Gln Val Ser Asp Ala Asp
    190                 195                 200 gga cgg atc agc aca gag ttc atg acg ttc agg atc gac agc gtt cgt              856
Gly Arg Ile Ser Thr Glu Phe Met Thr Phe Arg Ile Asp Ser Val Arg
205                 210                 215                 220 ggc gac gag gag acc ttc tac atc gaa cgg acg aat atc ccc aac caa              904
Gly Asp Glu Glu Thr Phe Tyr Ile Glu Arg Thr Asn Ile Pro Asn Gln
                225                 230                 235 tgg atg tgg cta aat atg acc ata ggc gtt aat acc tcg ctc aac ttc              952
Trp Met Trp Leu Asn Met Thr Ile Gly Val Asn Thr Ser Leu Asn Phe
            240                 245                 250 gtc acc agt ccg ctg cat ata ttc agc gtg aca gcc ctg gac tcg ctc             1000
Val Thr Ser Pro Leu His Ile Phe Ser Val Thr Ala Leu Asp Ser Leu
        255                 260                 265 ccg aac acc cac acg gtg act atg atg gtg caa gtg gcg aat gtg aac             1048
Pro Asn Thr His Thr Val Thr Met Met Val Gln Val Ala Asn Val Asn
    270                 275                 280 agc cgt ccg ccg cgc tgg ctg gag atc ttc gct gtc caa cag ttt gaa             1096
Ser Arg Pro Pro Arg Trp Leu Glu Ile Phe Ala Val Gln Gln Phe Glu
285                 290                 295                 300
```

```
gag aaa tct tac caa aac ttc aca gtg agg gcg atc gac gga gac act    1144
Glu Lys Ser Tyr Gln Asn Phe Thr Val Arg Ala Ile Asp Gly Asp Thr
            305                 310                 315 gag atc aat atg cct atc aac tac agg ctg atc aca aat gag gaa gac    1192
Glu Ile Asn Met Pro Ile Asn Tyr Arg Leu Ile Thr Asn Glu Glu Asp
        320                 325                 330 aca ttc ttc agc att gag gcc ctg cct ggt gga aaa agc ggg gct gta    1240
Thr Phe Phe Ser Ile Glu Ala Leu Pro Gly Gly Lys Ser Gly Ala Val
    335                 340                 345 ttc ctc gtg tcg cca att gac cgc gac aca ctg caa cga gag gtg ttt    1288
Phe Leu Val Ser Pro Ile Asp Arg Asp Thr Leu Gln Arg Glu Val Phe
350                 355                 360 cca ctt acg atc gtc gct tac aaa tat gat gag gag gcc ttc tcc aca    1336
Pro Leu Thr Ile Val Ala Tyr Lys Tyr Asp Glu Glu Ala Phe Ser Thr
365                 370                 375                 380 tca aca aac gtg gtc atc att gtg aca gac atc aac gac caa aga cct    1384
Ser Thr Asn Val Val Ile Ile Val Thr Asp Ile Asn Asp Gln Arg Pro
                385                 390                 395 gaa cct ata cac aag gaa tat cga ctg gca atc atg gag gag acg ccc    1432
Glu Pro Ile His Lys Glu Tyr Arg Leu Ala Ile Met Glu Glu Thr Pro
            400                 405                 410 ctg acc ctc aac ttc gat aaa gaa ttc gga ttt cat gat aag gat tta    1480
Leu Thr Leu Asn Phe Asp Lys Glu Phe Gly Phe His Asp Lys Asp Leu
        415                 420                 425 ggt caa aac gct cag tac acg gtg cgt cta gag agc gtg gac cct cca    1528
Gly Gln Asn Ala Gln Tyr Thr Val Arg Leu Glu Ser Val Asp Pro Pro
    430                 435                 440 ggc gct gct gag gca ttc tac ata gcg cct gaa gtc ggc tac cag cga    1576
Gly Ala Ala Glu Ala Phe Tyr Ile Ala Pro Glu Val Gly Tyr Gln Arg
445                 450                 455                 460 cag acc ttc atc atg ggc acc ctc aat cac tcc atg ctg gat tac gaa    1624
Gln Thr Phe Ile Met Gly Thr Leu Asn His Ser Met Leu Asp Tyr Glu
                465                 470                 475 gtg cca gag ttt cag agt att acg att cgg gtg gta gcg acc gac aac    1672
Val Pro Glu Phe Gln Ser Ile Thr Ile Arg Val Val Ala Thr Asp Asn
            480                 485                 490 aac gac acg agg cac gtg ggc gtc gcg ttg gtt cac att gac ctc atc    1720
Asn Asp Thr Arg His Val Gly Val Ala Leu Val His Ile Asp Leu Ile
        495                 500                 505 aat tgg aac gat gag cag ccg atc ttc gaa cac gcc gtg cag acc gtc    1768
Asn Trp Asn Asp Glu Gln Pro Ile Phe Glu His Ala Val Gln Thr Val
    510                 515                 520 acc ttc gac gag act gaa ggc gag ggg ttc ttc gtc gcc aag gcg gtt    1816
Thr Phe Asp Glu Thr Glu Gly Glu Gly Phe Phe Val Ala Lys Ala Val
525                 530                 535                 540 gca cac gac aga gac atc ggg gat gtc gtc gag cat act tta ttg ggt    1864
Ala His Asp Arg Asp Ile Gly Asp Val Val Glu His Thr Leu Leu Gly
                545                 550                 555
```

| | |
|---|---|
| aac gct gtt aac ttc ctg acc atc gac aaa ctc acc ggc gac atc cgc<br>Asn Ala Val Asn Phe Leu Thr Ile Asp Lys Leu Thr Gly Asp Ile Arg<br>          560                    565                    570 | 1912 |
| gtc tca gct aac gac tcc ttc aac tac cat cga gaa agt gaa tta ttt<br>Val Ser Ala Asn Asp Ser Phe Asn Tyr His Arg Glu Ser Glu Leu Phe<br>          575                    580                    585 | 1960 |
| gtg cag gtg cga gct aca gac acg ctg ggc gaa ccc ttc cac acg gcg<br>Val Gln Val Arg Ala Thr Asp Thr Leu Gly Glu Pro Phe His Thr Ala<br>          590                    595                    600 | 2008 |
| acg tca cag ctg gtc ata cga cta aat gac atc aac aac acg cca ccc<br>Thr Ser Gln Leu Val Ile Arg Leu Asn Asp Ile Asn Asn Thr Pro Pro<br>605                    610                    615                    620 | 2056 |
| acc tta cgg ctg cct cga ggc agt ccc caa gtg gag gag aac gtg cct<br>Thr Leu Arg Leu Pro Arg Gly Ser Pro Gln Val Glu Glu Asn Val Pro<br>          625                    630                    635 | 2104 |
| gat ggc cac gtc atc acc cag gag tta cgc gcc acc gac ccc gac acc<br>Asp Gly His Val Ile Thr Gln Glu Leu Arg Ala Thr Asp Pro Asp Thr<br>                640                    645                    650 | 2152 |
| acg gcc gat ctg cgc ttc gag ata aac tgg gac acc tct ttc gcc acc<br>Thr Ala Asp Leu Arg Phe Glu Ile Asn Trp Asp Thr Ser Phe Ala Thr<br>          655                    660                    665 | 2200 |
| aag caa ggc cgc cag gct aac ccc gac gag ttt agg aat tgc gtg gaa<br>Lys Gln Gly Arg Gln Ala Asn Pro Asp Glu Phe Arg Asn Cys Val Glu<br>          670                    675                    680 | 2248 |
| atc gag acc atc ttc ccc gag att aac aac cgg gga ctg gct atc ggc<br>Ile Glu Thr Ile Phe Pro Glu Ile Asn Asn Arg Gly Leu Ala Ile Gly<br>685                    690                    695                    700 | 2296 |
| cgc gtt gta gcg cgc gaa atc aga cac aac gtg acc ata gac tac gag<br>Arg Val Val Ala Arg Glu Ile Arg His Asn Val Thr Ile Asp Tyr Glu<br>          705                    710                    715 | 2344 |
| gag ttt gag gtc ctc tcc ctc aca gtg agg gtg cgt gac ctt aac acc<br>Glu Phe Glu Val Leu Ser Leu Thr Val Arg Val Arg Asp Leu Asn Thr<br>          720                    725                    730 | 2392 |
| gtc tac gga gac gac tac gac gaa tcg atg ctc aca ata act ata atc<br>Val Tyr Gly Asp Asp Tyr Asp Glu Ser Met Leu Thr Ile Thr Ile Ile<br>          735                    740                    745 | 2440 |
| gat atg aac gac aac gcg ccg gtg tgg gtg gag ggg act ctg gag cag<br>Asp Met Asn Asp Asn Ala Pro Val Trp Val Glu Gly Thr Leu Glu Gln<br>          750                    755                    760 | 2488 |
| aac ttc cga gtc cgc gag atg tcg gcg ggc ggg ctc gtg gtg ggc tcc<br>Asn Phe Arg Val Arg Glu Met Ser Ala Gly Gly Leu Val Val Gly Ser<br>765                    770                    775                    780 | 2536 |
| gtg cgc gcg gac gac atc gac gga ccg ctc tac aac caa gtg cga tac<br>Val Arg Ala Asp Asp Ile Asp Gly Pro Leu Tyr Asn Gln Val Arg Tyr<br>                785                    790                    795 | 2584 |
| acc att ttc cct cgt gaa gac aca gat aag gac ctg ata atg atc gac<br>Thr Ile Phe Pro Arg Glu Asp Thr Asp Lys Asp Leu Ile Met Ile Asp<br>          800                    805                    810 | 2632 |

```
ttc ctc acg ggt caa att tcc gtg aac aca agc ggc gcc atc gac gcg   2680
Phe Leu Thr Gly Gln Ile Ser Val Asn Thr Ser Gly Ala Ile Asp Ala
            815                 820                 825 gat act cct cca cgc ttc cac ctc tac tat aca gtg gtc gct agt gac   2728
Asp Thr Pro Pro Arg Phe His Leu Tyr Tyr Thr Val Val Ala Ser Asp
    830                 835                 840 cga tgc tcg aca gaa gat cct gca gat tgc ccc cct gac ccg act tat   2776
Arg Cys Ser Thr Glu Asp Pro Ala Asp Cys Pro Pro Asp Pro Thr Tyr
845                 850                 855                 860 tgg gaa acc gaa gga aat atc aca atc cac atc acc gac acg aac aac   2824
Trp Glu Thr Glu Gly Asn Ile Thr Ile His Ile Thr Asp Thr Asn Asn
                865                 870                 875 aag gtc ccg cag gcg gaa acg act aag ttc gat acc gtc gtg tat att   2872
Lys Val Pro Gln Ala Glu Thr Thr Lys Phe Asp Thr Val Val Tyr Ile
            880                 885                 890 tac gag aac gca acc cac tta gac gag gtg gtc act ctg ata gcc agt   2920
Tyr Glu Asn Ala Thr His Leu Asp Glu Val Val Thr Leu Ile Ala Ser
            895                 900                 905 gat ctt gac aga gac gaa ata tac cac acg gtg agc tac gtc atc aat   2968
Asp Leu Asp Arg Asp Glu Ile Tyr His Thr Val Ser Tyr Val Ile Asn
    910                 915                 920 tat gca gtg aac cct cga ctg atg aac ttc ttc tcc gtg aac cga gag   3016
Tyr Ala Val Asn Pro Arg Leu Met Asn Phe Phe Ser Val Asn Arg Glu
925                 930                 935                 940 acc ggc ctg gtg tac gtg gac tat gag acc cag ggt agt ggc gag gtg   3064
Thr Gly Leu Val Tyr Val Asp Tyr Glu Thr Gln Gly Ser Gly Glu Val
                945                 950                 955 ctg gac cgt gat ggt gat gaa cca acg cac cgt atc ttc ttc aac ctc   3112
Leu Asp Arg Asp Gly Asp Glu Pro Thr His Arg Ile Phe Phe Asn Leu
            960                 965                 970 atc gac aac ttc atg ggg gaa gga gaa ggt aac aga aat cag aac gac   3160
Ile Asp Asn Phe Met Gly Glu Gly Glu Gly Asn Arg Asn Gln Asn Asp
            975                 980                 985 aca gaa gtt ctc gtt atc ttg ttg gat gtg aat gac aat gct cct gaa   3208
Thr Glu Val Leu Val Ile Leu Leu Asp Val Asn Asp Asn Ala Pro Glu
    990                 995                 1000 ttg cca ccg ccg agc gaa ctc tct tgg act ata tct gag aac ctt aag   3256
Leu Pro Pro Pro Ser Glu Leu Ser Trp Thr Ile Ser Glu Asn Leu Lys
1005                1010                1015                1020 cag ggc gtc cgt ctt gaa cca cat atc ttc gcc ccg gac cgc gac gag   3304
Gln Gly Val Arg Leu Glu Pro His Ile Phe Ala Pro Asp Arg Asp Glu
                1025                1030                1035 ccc gac aca gac aac tcc agg gtc ggc tac gag atc ctg aac ctc agc   3352
Pro Asp Thr Asp Asn Ser Arg Val Gly Tyr Glu Ile Leu Asn Leu Ser
                1040                1045                1050 acg gag cgg gac atc gaa gtg ccg gag ctg ttt gtg atg ata cag atc   3400
Thr Glu Arg Asp Ile Glu Val Pro Glu Leu Phe Val Met Ile Gln Ile
```

```
                          -continued 1055                1060                1065 gcg aac gtc acg gga gag ctg gag acc gcc atg gac ctc aag gga tat     3448
Ala Asn Val Thr Gly Glu Leu Glu Thr Ala Met Asp Leu Lys Gly Tyr
     1070                1075                1080 tgg ggg acg tac gct ata cat ata cgg gca ttc gac cac ggc att ccg     3496
Trp Gly Thr Tyr Ala Ile His Ile Arg Ala Phe Asp His Gly Ile Pro
1085                1090                1095                1100 caa atg tcc atg aac gag aca tat gag ctg atc atc cat ccg ttc aac     3544
Gln Met Ser Met Asn Glu Thr Tyr Glu Leu Ile Ile His Pro Phe Asn
               1105                1110                1115 tac tac gcg cct gag ttc gtc ttc ccg acc aac gat gcc gtc ata cga     3592
Tyr Tyr Ala Pro Glu Phe Val Phe Pro Thr Asn Asp Ala Val Ile Arg
          1120                1125                1130 ctt gcg agg gaa cga gct gta atc aat gga gtt cta gcg aca gtg aac     3640
Leu Ala Arg Glu Arg Ala Val Ile Asn Gly Val Leu Ala Thr Val Asn
     1135                1140                1145 gga gag ttc ttg gag cgg ata tcg gcg act gat ccg gac gga ctc cac     3688
Gly Glu Phe Leu Glu Arg Ile Ser Ala Thr Asp Pro Asp Gly Leu His
1150                1155                1160 gcg ggc gtc gtc acc ttc caa gtg gta ggc gat gag gaa tca caa cgg     3736
Ala Gly Val Val Thr Phe Gln Val Val Gly Asp Glu Glu Ser Gln Arg
1165                1170                1175                1180 tac ttt caa gta gtt aac gat ggc gag aac ctc ggc tcg ttg agg tta     3784
Tyr Phe Gln Val Val Asn Asp Gly Glu Asn Leu Gly Ser Leu Arg Leu
               1185                1190                1195 ctg caa gcc gtt cca gag gag atc agg gag ttc cgg ata acg att cgc     3832
Leu Gln Ala Val Pro Glu Glu Ile Arg Glu Phe Arg Ile Thr Ile Arg
          1200                1205                1210 gct aca gac cag gga acg gac cca gga ccg ctg tcc acg gac atg acg     3880
Ala Thr Asp Gln Gly Thr Asp Pro Gly Pro Leu Ser Thr Asp Met Thr
     1215                1220                1225 ttc aga gtt gtt ttt gtg ccc acg caa gga gaa cct aga ttc gcg tcc     3928
Phe Arg Val Val Phe Val Pro Thr Gln Gly Glu Pro Arg Phe Ala Ser
1230                1235                1240 tca gaa cat gct gtc gct ttc ata gaa aag agt gcc ggc atg gaa gag     3976
Ser Glu His Ala Val Ala Phe Ile Glu Lys Ser Ala Gly Met Glu Glu
1245                1250                1255                1260 tct cac caa ctt cct cta gca caa gac atc aag aac cat ctc tgt gaa     4024
Ser His Gln Leu Pro Leu Ala Gln Asp Ile Lys Asn His Leu Cys Glu
               1265                1270                1275 gac gac tgt cac agc att tac tat cgt att atc gat ggc aac agc gaa     4072
Asp Asp Cys His Ser Ile Tyr Tyr Arg Ile Ile Asp Gly Asn Ser Glu
          1280                1285                1290 ggt cat ttc ggc ctg gat cct gtt cgc aac agg ttg ttc ctg aag aaa     4120
Gly His Phe Gly Leu Asp Pro Val Arg Asn Arg Leu Phe Leu Lys Lys
     1295                1300                1305 gag ctg ata agg gaa caa agt gcc tcc cac act ctg caa gtg gcg gct     4168
```

```
                                                          -continued

Glu Leu Ile Arg Glu Gln Ser Ala Ser His Thr Leu Gln Val Ala Ala
    1310                1315                1320 agt aac tcg ccc gat ggt ggc att cca ctt cct gct tcc atc ctt act    4216
Ser Asn Ser Pro Asp Gly Gly Ile Pro Leu Pro Ala Ser Ile Leu Thr
1325                1330                1335                1340 gtc act gtt acc gtg agg gag gca gac cct cgt cca gtg ttt gtg agg    4264
Val Thr Val Thr Val Arg Glu Ala Asp Pro Arg Pro Val Phe Val Arg
                1345                1350                1355 gaa ttg tac acc gca ggg ata tcc aca gcg gac tcc atc ggc aga gag    4312
Glu Leu Tyr Thr Ala Gly Ile Ser Thr Ala Asp Ser Ile Gly Arg Glu
        1360                1365                1370 ctg ctc aga tta cat gcg acc cag tct gaa ggc tcg gcc att act tat    4360
Leu Leu Arg Leu His Ala Thr Gln Ser Glu Gly Ser Ala Ile Thr Tyr
    1375                1380                1385 gct ata gac tac gat aca atg gta gtg gac ccc agc ctg gag gca gtg    4408
Ala Ile Asp Tyr Asp Thr Met Val Val Asp Pro Ser Leu Glu Ala Val
1390                1395                1400 aga cag tcg gct ttc gta ctg aac gct caa acc gga gtg ctg acg ctt    4456
Arg Gln Ser Ala Phe Val Leu Asn Ala Gln Thr Gly Val Leu Thr Leu
1405                1410                1415                1420 aat atc cag ccc acg gcc acg atg cat gga ctg ttc aaa ttc gaa gtc    4504
Asn Ile Gln Pro Thr Ala Thr Met His Gly Leu Phe Lys Phe Glu Val
                1425                1430                1435 aca gct act gac acg gcc ggc gct cag gac cgc acc gac gtc acc gtg    4552
Thr Ala Thr Asp Thr Ala Gly Ala Gln Asp Arg Thr Asp Val Thr Val
        1440                1445                1450 tac gtg gta tcc tcg cag aac cgc gtc tac ttc gtg ttc gtc aac acg    4600
Tyr Val Val Ser Ser Gln Asn Arg Val Tyr Phe Val Phe Val Asn Thr
    1455                1460                1465 ctg caa cag gtc gaa gac aac aga gac ttt atc gcg gac acc ttc agc    4648
Leu Gln Gln Val Glu Asp Asn Arg Asp Phe Ile Ala Asp Thr Phe Ser
1470                1475                1480 gct ggg ttc aac atg acc tgc aac atc gac caa gtg gtg ccc gct aac    4696
Ala Gly Phe Asn Met Thr Cys Asn Ile Asp Gln Val Val Pro Ala Asn
1485                1490                1495                1500 gac ccc gtc acc ggc gtg gcg ctg gag cac agc acg cag atg cgc ggc    4744
Asp Pro Val Thr Gly Val Ala Leu Glu His Ser Thr Gln Met Arg Gly
                1505                1510                1515 cac ttc ata cgg gac aac gta ccc gta ctc gct gat gag ata gaa cag    4792
His Phe Ile Arg Asp Asn Val Pro Val Leu Ala Asp Glu Ile Glu Gln
        1520                1525                1530 atc cgt agt gac cta gtc ctc ctg agc tcg ata caa aca acg ctg gcg    4840
Ile Arg Ser Asp Leu Val Leu Leu Ser Ser Ile Gln Thr Thr Leu Ala
    1535                1540                1545 gcg cga tcg ctg gtg ttg cag gac ttg ttg acc aac tcc agc ccg gac    4888
Ala Arg Ser Leu Val Leu Gln Asp Leu Leu Thr Asn Ser Ser Pro Asp
1550                1555                1560
```

-continued

```
tcg gcg cct gac tcg agc ctc acg gtg tac gtg ctg gcc tca ctg tct      4936
Ser Ala Pro Asp Ser Ser Leu Thr Val Tyr Val Leu Ala Ser Leu Ser
1565                1570                1575                1580 gct gtg ctc ggt ttc atg tgc ctt gtg cta ctg ctt acc ttc atc atc      4984
Ala Val Leu Gly Phe Met Cys Leu Val Leu Leu Leu Thr Phe Ile Ile
                1585                1590                1595 agg act aga gcg cta aac cga cgg ttg gaa gcc ctg tcg atg acg aag      5032
Arg Thr Arg Ala Leu Asn Arg Arg Leu Glu Ala Leu Ser Met Thr Lys
1600                1605                1610 tac ggc tca ctg gac tct gga ttg aac cgc gcc ggc atc gcc gcc ccc      5080
Tyr Gly Ser Leu Asp Ser Gly Leu Asn Arg Ala Gly Ile Ala Ala Pro
                1615                1620                1625 ggc acc aac aaa cac act gtg gaa ggc tcc aac cct atc ttc aat gaa      5128
Gly Thr Asn Lys His Thr Val Glu Gly Ser Asn Pro Ile Phe Asn Glu
1630                1635                1640 gca ata aag acg cca gat tta gat gcc att agc gag ggt tcc aac gac      5176
Ala Ile Lys Thr Pro Asp Leu Asp Ala Ile Ser Glu Gly Ser Asn Asp
1645                1650                1655                1660 tct gat ctg atc ggc atc gaa gat ctt ccg cac ttt ggc aac gtc ttc      5224
Ser Asp Leu Ile Gly Ile Glu Asp Leu Pro His Phe Gly Asn Val Phe
                1665                1670                1675 atg gat cct gag gtg aac gaa aag gca aat ggt tat ccc gaa gtc gca      5272
Met Asp Pro Glu Val Asn Glu Lys Ala Asn Gly Tyr Pro Glu Val Ala
1680                1685                1690 aac cac aac aac aac ttc gct ttc aac ccg act ccc ttc tcg cct gag      5320
Asn His Asn Asn Asn Phe Ala Phe Asn Pro Thr Pro Phe Ser Pro Glu
                1695                1700                1705 ttc gtt aac gga cag ttc aga aag atc t agaagataac aacactagtt          5368
Phe Val Asn Gly Gln Phe Arg Lys Ile
    1710                1715 aagatcatta attttggagt ttggaattaa gattttgaa aggatagttg tgataagcct     5428 gtgatttta aaactgtaat tgaaaaaaaa aattgagacc tccatttaag ctcttgctct     5488
catctcatca aatttataa aatgccatta gtcattaaga tactcgattt aatttaagat     5548
tatttaagat attatgtaaa ataaatatat tgtc                                5582
```

<210> SEQ ID NO 2
<211> LENGTH: 1717
<212> TYPE: PRT
<213> ORGANISM: M. sexta

<400> SEQUENCE: 2

```
Met Ala Val Asp Val Arg Ile Ala Ala Phe Leu Leu Val Phe Ile Ala
 1               5                  10                  15

Pro Ala Val Leu Ala Gln Glu Arg Cys Gly Tyr Met Thr Ala Ile Pro
            20                  25                  30

Arg Leu Pro Arg Pro Asp Asn Leu Pro Val Leu Asn Phe Glu Gly Gln
        35                  40                  45

Thr Trp Ser Gln Arg Pro Leu Leu Pro Ala Pro Glu Arg Asp Asp Leu
    50                  55                  60

Cys Met Asp Ala Tyr His Val Ile Thr Ala Asn Leu Gly Thr Gln Val
65                  70                  75                  80
```

```
Ile Tyr Met Asp Glu Glu Ile Glu Asp Glu Ile Thr Ile Ala Ile Leu
                85                  90                  95

Asn Tyr Asn Gly Pro Ser Thr Pro Phe Ile Glu Leu Pro Phe Leu Ser
            100                 105                 110

Gly Ser Tyr Asn Leu Leu Met Pro Val Ile Arg Arg Val Asp Asn Gly
        115                 120                 125

Glu Trp His Leu Ile Ile Thr Gln Arg Gln His Tyr Glu Leu Pro Gly
    130                 135                 140

Met Gln Gln Tyr Met Phe Asn Val Arg Val Asp Gly Gln Ser Leu Val
145                 150                 155                 160

Ala Gly Val Ser Leu Ala Ile Val Asn Ile Asp Asp Asn Ala Pro Ile
                165                 170                 175

Ile Gln Asn Phe Glu Pro Cys Arg Val Pro Glu Leu Gly Glu Pro Gly
            180                 185                 190

Leu Thr Glu Cys Thr Tyr Gln Val Ser Asp Ala Asp Gly Arg Ile Ser
        195                 200                 205

Thr Glu Phe Met Thr Phe Arg Ile Asp Ser Val Arg Gly Asp Glu Glu
    210                 215                 220

Thr Phe Tyr Ile Glu Arg Thr Asn Ile Pro Asn Gln Trp Met Trp Leu
225                 230                 235                 240

Asn Met Thr Ile Gly Val Asn Thr Ser Leu Asn Phe Val Thr Ser Pro
                245                 250                 255

Leu His Ile Phe Ser Val Thr Ala Leu Asp Ser Leu Pro Asn Thr His
            260                 265                 270

Thr Val Thr Met Met Val Gln Val Ala Asn Val Asn Ser Arg Pro Pro
        275                 280                 285

Arg Trp Leu Glu Ile Phe Ala Val Gln Gln Phe Glu Glu Lys Ser Tyr
    290                 295                 300

Gln Asn Phe Thr Val Arg Ala Ile Asp Gly Asp Thr Glu Ile Asn Met
305                 310                 315                 320

Pro Ile Asn Tyr Arg Leu Ile Thr Asn Glu Glu Asp Thr Phe Phe Ser
                325                 330                 335

Ile Glu Ala Leu Pro Gly Gly Lys Ser Gly Ala Val Phe Leu Val Ser
            340                 345                 350

Pro Ile Asp Arg Asp Thr Leu Gln Arg Glu Val Phe Pro Leu Thr Ile
        355                 360                 365

Val Ala Tyr Lys Tyr Asp Glu Glu Ala Phe Ser Thr Ser Thr Asn Val
    370                 375                 380

Val Ile Ile Val Thr Asp Ile Asn Asp Gln Arg Pro Glu Pro Ile His
385                 390                 395                 400

Lys Glu Tyr Arg Leu Ala Ile Met Glu Glu Thr Pro Leu Thr Leu Asn
                405                 410                 415

Phe Asp Lys Glu Phe Gly Phe His Asp Lys Asp Leu Gly Gln Asn Ala
            420                 425                 430

Gln Tyr Thr Val Arg Leu Glu Ser Val Asp Pro Pro Gly Ala Ala Glu
        435                 440                 445

Ala Phe Tyr Ile Ala Pro Glu Val Gly Tyr Gln Arg Gln Thr Phe Ile
    450                 455                 460

Met Gly Thr Leu Asn His Ser Met Leu Asp Tyr Glu Val Pro Glu Phe
465                 470                 475                 480

Gln Ser Ile Thr Ile Arg Val Val Ala Thr Asp Asn Asn Asp Thr Arg
                485                 490                 495
```

-continued

```
His Val Gly Val Ala Leu Val His Ile Asp Leu Ile Asn Trp Asn Asp
            500                 505                 510
Glu Gln Pro Ile Phe Glu His Ala Val Gln Thr Val Thr Phe Asp Glu
            515                 520                 525
Thr Glu Gly Glu Gly Phe Phe Val Ala Lys Ala Val Ala His Asp Arg
            530                 535                 540
Asp Ile Gly Asp Val Val Glu His Thr Leu Leu Gly Asn Ala Val Asn
545                 550                 555                 560
Phe Leu Thr Ile Asp Lys Leu Thr Gly Asp Ile Arg Val Ser Ala Asn
                565                 570                 575
Asp Ser Phe Asn Tyr His Arg Glu Ser Glu Leu Phe Val Gln Val Arg
            580                 585                 590
Ala Thr Asp Thr Leu Gly Glu Pro Phe His Thr Ala Thr Ser Gln Leu
            595                 600                 605
Val Ile Arg Leu Asn Asp Ile Asn Asn Thr Pro Pro Thr Leu Arg Leu
            610                 615                 620
Pro Arg Gly Ser Pro Gln Val Glu Glu Asn Val Pro Asp Gly His Val
625                 630                 635                 640
Ile Thr Gln Glu Leu Arg Ala Thr Asp Pro Asp Thr Ala Asp Leu
                645                 650                 655
Arg Phe Glu Ile Asn Trp Asp Thr Ser Phe Ala Thr Lys Gln Gly Arg
            660                 665                 670
Gln Ala Asn Pro Asp Glu Phe Arg Asn Cys Val Glu Ile Glu Thr Ile
            675                 680                 685
Phe Pro Glu Ile Asn Asn Arg Gly Leu Ala Ile Gly Arg Val Val Ala
            690                 695                 700
Arg Glu Ile Arg His Asn Val Thr Ile Asp Tyr Glu Glu Phe Glu Val
705                 710                 715                 720
Leu Ser Leu Thr Val Arg Val Arg Asp Leu Asn Thr Val Tyr Gly Asp
                725                 730                 735
Asp Tyr Asp Glu Ser Met Leu Thr Ile Thr Ile Asp Met Asn Asp
            740                 745                 750
Asn Ala Pro Val Trp Val Glu Gly Thr Leu Glu Gln Asn Phe Arg Val
            755                 760                 765
Arg Glu Met Ser Ala Gly Gly Leu Val Val Gly Ser Val Arg Ala Asp
            770                 775                 780
Asp Ile Asp Gly Pro Leu Tyr Asn Gln Val Arg Tyr Thr Ile Phe Pro
785                 790                 795                 800
Arg Glu Asp Thr Asp Lys Asp Leu Ile Met Ile Asp Phe Leu Thr Gly
                805                 810                 815
Gln Ile Ser Val Asn Thr Ser Gly Ala Ile Asp Ala Asp Thr Pro Pro
            820                 825                 830
Arg Phe His Leu Tyr Tyr Thr Val Ala Ser Asp Arg Cys Ser Thr
            835                 840                 845
Glu Asp Pro Ala Asp Cys Pro Pro Asp Pro Thr Tyr Trp Glu Thr Glu
850                 855                 860
Gly Asn Ile Thr Ile His Ile Thr Asp Thr Asn Asn Lys Val Pro Gln
865                 870                 875                 880
Ala Glu Thr Thr Lys Phe Asp Thr Val Val Tyr Ile Tyr Glu Asn Ala
                885                 890                 895
Thr His Leu Asp Glu Val Val Thr Leu Ile Ala Ser Asp Leu Asp Arg
            900                 905                 910
Asp Glu Ile Tyr His Thr Val Ser Tyr Val Ile Asn Tyr Ala Val Asn
```

-continued

Pro Arg Leu Met Asn Phe Phe Ser Val Asn Arg Glu Thr Gly Leu Val
915                 920                 925
930                 935                 940

Tyr Val Asp Tyr Glu Thr Gln Gly Ser Gly Val Leu Asp Arg Asp
945                 950                 955                 960

Gly Asp Glu Pro Thr His Arg Ile Phe Phe Asn Leu Ile Asp Asn Phe
                965                 970                 975

Met Gly Glu Gly Glu Gly Asn Arg Asn Gln Asn Asp Thr Glu Val Leu
            980                 985                 990

Val Ile Leu Leu Asp Val Asn Asp Asn Ala Pro Glu Leu Pro Pro Pro
                995                 1000                1005

Ser Glu Leu Ser Trp Thr Ile Ser Glu Asn Leu Lys Gln Gly Val Arg
    1010                1015                1020

Leu Glu Pro His Ile Phe Ala Pro Asp Arg Asp Glu Pro Asp Thr Asp
1025                1030                1035                1040

Asn Ser Arg Val Gly Tyr Glu Ile Leu Asn Leu Ser Thr Glu Arg Asp
                1045                1050                1055

Ile Glu Val Pro Glu Leu Phe Val Met Ile Gln Ile Ala Asn Val Thr
                1060                1065                1070

Gly Glu Leu Glu Thr Ala Met Asp Leu Lys Gly Tyr Trp Gly Thr Tyr
                1075                1080                1085

Ala Ile His Ile Arg Ala Phe Asp His Gly Ile Pro Gln Met Ser Met
            1090                1095                1100

Asn Glu Thr Tyr Glu Leu Ile Ile His Pro Phe Asn Tyr Tyr Ala Pro
1105                1110                1115                1120

Glu Phe Val Phe Pro Thr Asn Asp Ala Val Ile Arg Leu Ala Arg Glu
                1125                1130                1135

Arg Ala Val Ile Asn Gly Val Leu Ala Thr Val Asn Gly Glu Phe Leu
                1140                1145                1150

Glu Arg Ile Ser Ala Thr Asp Pro Asp Gly Leu His Ala Gly Val Val
            1155                1160                1165

Thr Phe Gln Val Val Gly Asp Glu Glu Ser Gln Arg Tyr Phe Gln Val
    1170                1175                1180

Val Asn Asp Gly Glu Asn Leu Gly Ser Leu Arg Leu Leu Gln Ala Val
1185                1190                1195                1200

Pro Glu Glu Ile Arg Glu Phe Arg Ile Thr Ile Arg Ala Thr Asp Gln
                1205                1210                1215

Gly Thr Asp Pro Gly Pro Leu Ser Thr Asp Met Thr Phe Arg Val Val
            1220                1225                1230

Phe Val Pro Thr Gln Gly Glu Pro Arg Phe Ala Ser Ser Glu His Ala
    1235                1240                1245

Val Ala Phe Ile Glu Lys Ser Ala Gly Met Glu Glu Ser His Gln Leu
    1250                1255                1260

Pro Leu Ala Gln Asp Ile Lys Asn His Leu Cys Glu Asp Cys His
1265                1270                1275                1280

Ser Ile Tyr Tyr Arg Ile Ile Asp Gly Asn Ser Glu Gly His Phe Gly
                1285                1290                1295

Leu Asp Pro Val Arg Asn Arg Leu Phe Leu Lys Lys Glu Leu Ile Arg
            1300                1305                1310

Glu Gln Ser Ala Ser His Thr Leu Gln Val Ala Ala Ser Asn Ser Pro
    1315                1320                1325

Asp Gly Gly Ile Pro Leu Pro Ala Ser Ile Leu Thr Val Thr Val Thr
            1330                1335                1340

-continued

Val Arg Glu Ala Asp Pro Arg Pro Val Phe Val Arg Glu Leu Tyr Thr
1345                1350                1355                1360

Ala Gly Ile Ser Thr Ala Asp Ser Ile Gly Arg Glu Leu Leu Arg Leu
            1365                1370                1375

His Ala Thr Gln Ser Glu Gly Ser Ala Ile Thr Tyr Ala Ile Asp Tyr
        1380                1385                1390

Asp Thr Met Val Val Asp Pro Ser Leu Glu Ala Val Arg Gln Ser Ala
    1395                1400                1405

Phe Val Leu Asn Ala Gln Thr Gly Val Leu Thr Leu Asn Ile Gln Pro
        1410                1415                1420

Thr Ala Thr Met His Gly Leu Phe Lys Phe Glu Val Thr Ala Thr Asp
1425                1430                1435                1440

Thr Ala Gly Ala Gln Asp Arg Thr Asp Val Thr Val Tyr Val Val Ser
            1445                1450                1455

Ser Gln Asn Arg Val Tyr Phe Val Phe Val Asn Thr Leu Gln Gln Val
        1460                1465                1470

Glu Asp Asn Arg Asp Phe Ile Ala Asp Thr Phe Ser Ala Gly Phe Asn
    1475                1480                1485

Met Thr Cys Asn Ile Asp Gln Val Val Pro Ala Asn Asp Pro Val Thr
        1490                1495                1500

Gly Val Ala Leu Glu His Ser Thr Gln Met Arg Gly His Phe Ile Arg
1505                1510                1515                1520

Asp Asn Val Pro Val Leu Ala Asp Glu Ile Glu Gln Ile Arg Ser Asp
            1525                1530                1535

Leu Val Leu Leu Ser Ser Ile Gln Thr Thr Leu Ala Ala Arg Ser Leu
        1540                1545                1550

Val Leu Gln Asp Leu Leu Thr Asn Ser Ser Pro Asp Ser Ala Pro Asp
    1555                1560                1565

Ser Ser Leu Thr Val Tyr Val Leu Ala Ser Leu Ser Ala Val Leu Gly
        1570                1575                1580

Phe Met Cys Leu Val Leu Leu Thr Phe Ile Ile Arg Thr Arg Ala
1585                1590                1595                1600

Leu Asn Arg Arg Leu Glu Ala Leu Ser Met Thr Lys Tyr Gly Ser Leu
            1605                1610                1615

Asp Ser Gly Leu Asn Arg Ala Gly Ile Ala Ala Pro Gly Thr Asn Lys
        1620                1625                1630

His Thr Val Glu Gly Ser Asn Pro Ile Phe Asn Glu Ala Ile Lys Thr
    1635                1640                1645

Pro Asp Leu Asp Ala Ile Ser Glu Gly Ser Asn Asp Ser Asp Leu Ile
    1650                1655                1660

Gly Ile Glu Asp Leu Pro His Phe Gly Asn Val Phe Met Asp Pro Glu
1665                1670                1675                1680

Val Asn Glu Lys Ala Asn Gly Tyr Pro Glu Val Ala Asn His Asn Asn
            1685                1690                1695

Asn Phe Ala Phe Asn Pro Thr Pro Phe Ser Pro Glu Phe Val Asn Gly
        1700                1705                1710

Gln Phe Arg Lys Ile
        1715

<210> SEQ ID NO 3
<211> LENGTH: 30
<212> TYPE: PRT
<213> ORGANISM: M. sexta

```
<400> SEQUENCE: 3

Met Leu Asp Tyr Glu Val Pro Glu Phe Gln Ser Ile Thr Ile Arg Val
 1               5                  10                  15

Val Ala Thr Asp Asn Asn Asp Thr Arg His Val Gly Val Ala
            20                  25                  30

<210> SEQ ID NO 4
<211> LENGTH: 16
<212> TYPE: PRT
<213> ORGANISM: M. sexta
<220> FEATURE:
<221> NAME/KEY: VARIANT
<222> LOCATION: (1)...(16)
<223> OTHER INFORMATION: Xaa = Any Amino Acid

<400> SEQUENCE: 4

Met Xaa Glu Thr Tyr Glu Leu Ile Ile His Pro Phe Asn Tyr Tyr Ala
 1               5                  10                  15

<210> SEQ ID NO 5
<211> LENGTH: 16
<212> TYPE: PRT
<213> ORGANISM: M. sexta
<220> FEATURE:
<221> NAME/KEY: VARIANT
<222> LOCATION: (1)...(16)
<223> OTHER INFORMATION: Xaa = Any Amino Acid

<400> SEQUENCE: 5

Met Xaa Xaa Xaa His Gln Leu Pro Leu Ala Gln Asp Ile Lys Asn His
 1               5                  10                  15

<210> SEQ ID NO 6
<211> LENGTH: 8
<212> TYPE: PRT
<213> ORGANISM: M. sexta
<220> FEATURE:
<221> NAME/KEY: VARIANT
<222> LOCATION: (1)...(8)
<223> OTHER INFORMATION: Xaa = Any Amino Acid

<400> SEQUENCE: 6

Met Xaa Xaa Val Xaa Val Asp Xaa
 1               5

<210> SEQ ID NO 7
<211> LENGTH: 9
<212> TYPE: PRT
<213> ORGANISM: M. sexta
<220> FEATURE:
<221> NAME/KEY: VARIANT
<222> LOCATION: (1)...(9)
<223> OTHER INFORMATION: Xaa = Any Amino Acid

<400> SEQUENCE: 7

Met Asn Phe Xaa Ser Val Asn Xaa Glu
 1               5

<210> SEQ ID NO 8
<211> LENGTH: 109
<212> TYPE: PRT
<213> ORGANISM: Mouse

<400> SEQUENCE: 8

Glu Trp Val Met Pro Pro Ile Phe Val Pro Glu Asn Gly Lys Gly Pro
 1               5                  10                  15
```

Phe Pro Gln Arg Leu Asn Gln Leu Lys Ser Asn Lys Asp Arg Gly Thr
                20                  25                  30

Lys Ile Phe Tyr Tyr Ser Ile Thr Gly Pro Gly Ala Asp Ser Pro Pro
            35                  40                  45

Glu Gly Val Phe Thr Ile Glu Lys Glu Ser Gly Trp Leu Leu Leu His
    50                  55                  60

Met Pro Leu Asp Arg Glu Lys Ile Val Lys Tyr Glu Leu Tyr Gly His
65                  70                  75                  80

Ala Val Ser Glu Asn Gly Ala Ser Val Glu Glu Pro Met Asn Ile Ser
                85                  90                  95

Ile Ile Val Thr Asp Gln Asn Asp Asn Lys Pro Lys Phe
                100                 105

<210> SEQ ID NO 9
<211> LENGTH: 105
<212> TYPE: PRT
<213> ORGANISM: Drosophila

<400> SEQUENCE: 9

Glu Asp Thr Val Tyr Ser Phe Asp Ile Asp Glu Asn Ala Gln Arg Gly
1               5                   10                  15

Tyr Gln Val Gly Gln Ile Val Ala Arg Asp Ala Asp Leu Gly Gln Asn
                20                  25                  30

Ala Gln Leu Ser Tyr Gly Val Val Ser Asp Trp Ala Asn Asp Val Phe
            35                  40                  45

Ser Leu Asn Pro Gln Thr Gly Met Leu Thr Leu Thr Ala Arg Leu Asp
    50                  55                  60

Tyr Glu Val Gln His Tyr Ile Leu Ile Val Gln Ala Gln Asp Asn
65                  70                  75                  80

Gly Gln Pro Ser Leu Ser Thr Thr Ile Thr Val Tyr Cys Asn Val Leu
                85                  90                  95

Asp Leu Asn Asp Asn Ala Pro Ile Phe
                100                 105

<210> SEQ ID NO 10
<211> LENGTH: 92
<212> TYPE: PRT
<213> ORGANISM: Protocadherin

<400> SEQUENCE: 10

Ala Ser Pro Val Ile Thr Leu Ala Ile Pro Glu Asn Thr Asn Gly Ser
1               5                   10                  15

Leu Phe Pro Ile Pro Leu Ala Ser Asp Arg Asp Ala Asn Glu Leu Gln
                20                  25                  30

Val Ala Glu Asp Gln Glu Glu Lys Gln Pro Gln Leu Ile Val Met Gly
            35                  40                  45

Asn Leu Asp Arg Glu Arg Trp Asp Ser Tyr Asp Leu Thr Ile Lys Val
    50                  55                  60

Gln Asp Gly Gly Ser Pro Pro Arg Ala Thr Ser Ala Leu Leu Arg Val
65                  70                  75                  80

Thr Val Leu Asp Thr Asn Asp Asn Ala Pro Lys Phe
                85                  90

<210> SEQ ID NO 11
<211> LENGTH: 106
<212> TYPE: PRT
<213> ORGANISM: M. sexta

```
<400> SEQUENCE: 11

Ile Val Thr Glu Asn Ile Trp Lys Ala Pro Lys Pro Val Glu Met Val
1               5                   10                  15
Glu Asn Ser Thr Pro His Pro Ile Lys Ile Thr Gln Val Arg Trp Asn
            20                  25                  30
Asp Pro Gly Ala Gln Tyr Ser Leu Val Asp Lys Glu Lys Leu Pro Arg
        35                  40                  45
Phe Pro Phe Ser Ile Asp Gln Glu Gly Asp Ile Tyr Val Thr Gln Pro
    50                  55                  60
Ile Asp Arg Glu Glu Lys Asp Ala Tyr Val Phe Tyr Ala Val Ala Lys
65                  70                  75                  80
Asp Glu Tyr Gly Lys Pro Leu Ser Tyr Pro Leu Glu Ile His Val Lys
                85                  90                  95
Val Lys Asp Asn Asp Asn Pro Pro Thr Cys
                100                 105

<210> SEQ ID NO 12
<211> LENGTH: 5
<212> TYPE: PRT
<213> ORGANISM: M. sexta
<220> FEATURE:
<221> NAME/KEY: VARIANT
<222> LOCATION: (1)...(5)
<223> OTHER INFORMATION: Xaa = Any Amino Acid

<400> SEQUENCE: 12

Ala Xaa Asp Xaa Asp
1               5

<210> SEQ ID NO 13
<211> LENGTH: 7
<212> TYPE: PRT
<213> ORGANISM: M. sexta
<220> FEATURE:
<221> NAME/KEY: VARIANT
<222> LOCATION: (1)...(7)
<223> OTHER INFORMATION: Xaa = Any Amino Acid

<400> SEQUENCE: 13

Asp Xaa Asn Asp Xaa Xaa Pro
1               5

<210> SEQ ID NO 14
<211> LENGTH: 5
<212> TYPE: PRT
<213> ORGANISM: M. sexta
<220> FEATURE:
<221> NAME/KEY: VARIANT
<222> LOCATION: (1)...(5)
<223> OTHER INFORMATION: Xaa = Any Amino Acid

<400> SEQUENCE: 14

Xaa Xaa Asp Xaa Asp
1               5

<210> SEQ ID NO 15
<211> LENGTH: 5
<212> TYPE: PRT
<213> ORGANISM: M. sexta
<220> FEATURE:
<221> NAME/KEY: VARIANT
<222> LOCATION: (1)...(5)
<223> OTHER INFORMATION: Xaa = Any Amino Acid
```

-continued

```
<400> SEQUENCE: 15

Asp Xaa Asn Asp Asn
1               5
```

RECEPTOR FOR A *BACILLUS THURINGIENSIS* TOXIN

RELATED APPLICATIONS

This application is a divisional of application Ser. No. 08/880,042, filed Jun. 20, 1997, still pending; which is a continuation-in-part of application Ser. No. 08/326,117 filed Oct. 19, 1994, now U.S. Pat. No. 5,693,491.

ACKNOWLEDGMENT OF GOVERNMENT SUPPORT

Work resulting in the present invention was supported in part by Research Agreement 58-319R-3-011 from the Office of International Cooperation and Development, U.S.D.A. and by Cooperative Agreement 58-5410-1-135 from the Arthropod-Borne Animal Disease Laboratory, Agricultural Research Service, U.S.D.A. and by Grant HD-18702 from the National Institutes of Health. The U.S. government has certain rights in this invention.

TECHNICAL FIELD

The invention relates to receptors that bind toxins from *Bacillus thuringiensis* and thus to pesticides and pest resistance. More particularly, the invention concerns recombinantly produced receptors that bind BT toxin and to their use in assays for improved pesticides, as well as in mediation of cell and tissue destruction, dissociation, dispersion, cell-to-cell association, and changes in morphology.

BACKGROUND ART

It has long been recognized that the bacterium *Bacillus thuringiensis* (BT) produces bactericidal proteins that are toxic to a limited range of insects, mostly in the orders Lepidoptera, Coleoptera and Diptera. Advantage has been taken of these toxins in controlling pests, mostly by applying bacteria to plants or transforming plants themselves so that they generate the toxins by virtue of their transgenic character. The toxins themselves are glycoprotein products of the cry gene as described by Höfte, H. et al. *Microbiol Rev* (1989) 53:242. It has been established that the toxins function in the brush border of the insect midgut epithelial cells as described by Gill, S. S. et al. *Annu Rev Entomol* (1992) 37:615. Specific binding of BT toxins to midgut brush border membrane vesicles has been reported by Hofmann, C. et al. *Proc Natl Acad Sci USA* (1988) 85:7844; Van Rie, J. et al. *Eur J Biochem* (1989) 186:239; and Van Rie, J. et al. *Appl Environ Microbiol* (1990) 56:1378.

Presumably, the toxins generated by BT exert their effects by some kind of interaction with receptors in the midgut. The purification of a particular receptor from *Manduca sexta* was reported by the present inventors in an article by Vadlamudi, R. K. et al. *J Biol Chem* (1993) 268:12334. In this report, the receptor protein was isolated by immunoprecipitating toxin-binding protein complexes with toxin-specific antisera and separating the complexes by SDS-PAGE followed by electroelution. However, to date, there has been no structural information concerning any insect receptor which binds BT toxin, nor have, to applicants' knowledge, any genes encoding these receptors been recovered.

DISCLOSURE OF THE INVENTION

The present invention is based, in part, on the isolation and characterization of a receptor that is bound by members of the BT-toxin family of insecticidal proteins, hereinafter the BT-$R_1$ protein. The present invention is further based on the isolation and characterization of a nucleic acid molecule that encodes the BT-toxin receptor, hereinafter BT-$R_1$ gene. Based on these observations, the present invention provides compositions and methods for use in identifying agents that bind to the BT-$R_1$ protein as a means for identifying insecticidal agent and for identifying other members of the BT-$R_1$ family of proteins.

BRIEF DESCRIPTION OF THE DRAWINGS

FIGS. 1A–1M show the nucleotide sequence (SEQ ID NO:1) and deduced amino acid sequence (SEQ ID NO:2) of cDNA encoding the BT-$R_1$ protein from *M. sexta*.

FIGS. 2A–2H show the deduced amino acid sequence of cDNA encoding the BT-$R_1$ protein from *M. sexta* (SEQ ID NO:2). FIG. 2I shows a comparison of amino acid sequences of cadherin motifs (BTRcad-1 to 11) in BT-$R_1$ to those of other cadherins (SEQ ID NOS:8–11).

MODES OF CARRYING OUT THE INVENTION

I. General Description

Figure 3:
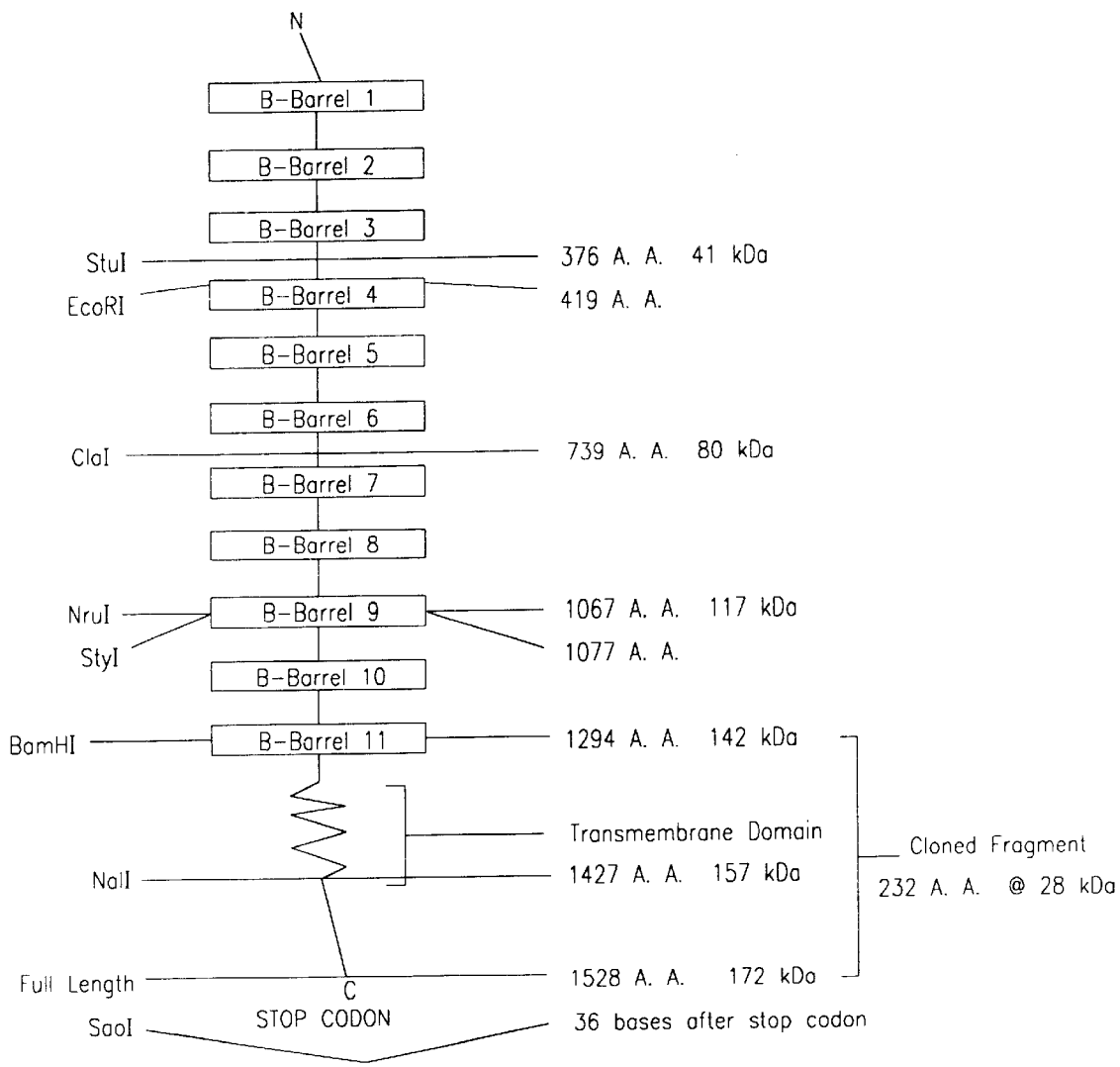
FIG. 3 shows a block diagram of the cadherin-like structure of BT-$R_1$.

The present invention is based, in part, on the isolation and characterization of a novel protein expressed in the midgut of *Manduca sexta* that binds to members of the BT-toxin family of proteins, hereinafter the BT-$R_1$ protein. The present invention specifically provides purified BT-$R_1$ the amino acid sequence of BT-$R_1$, as well as nucleotide sequences that encode BT-$R_1$. The BT-$R_1$ protein and nucleic acid molecules can serve as targets in identifying insecticidal agents.

II. Specific Embodiments

A. BT-R$_1$ Protein

Prior to the present invention, although members of the BT-toxin family of protein were known, no one had identified the receptor that is bound by these toxin proteins. The present invention provides, in part, the amino acid sequences of a BT-toxin receptor that is expressed in the midgut of *Manduca sexta*.

In one embodiment, the present invention provides the ability to isolate or produce a previously unknown protein by using known purification methods, the cloned nucleic acid molecules herein described or by synthesizing a protein having the amino acid sequence herein disclosed.

As used herein, BT-R$_1$ refers to a protein that has the amino acid sequence of BT-R$_1$ provided in FIG. 1, as well as allelic variants of the BT-R$_1$ sequence, and conservative substitutions mutants of the BT-R$_1$ sequence that have BT-R$_1$ activity. BT-R$_1$ is comprised of a single subunit, has a molecular weight of 210 kD, and has the amino acid sequence provided in FIG. 1. A prediction of the structure of BT-R$_1$ is provided in FIG. 3.

The BT-R$_1$ protein of the present invention includes the specifically identified and characterized variant herein described, as well as allelic variants, conservative substitution variants and homologues (FIG. 7) that can be isolated/generated and characterized without undue experimentation following the methods outlined below. For the sake of convenience, all BT-R$_1$ proteins will be collectively referred to as the BT-R$_1$ proteins, the BT-R$_1$ proteins of the present invention or BT-R$_1$.

The term "BT-R$_1$" includes all naturally occurring allelic variants of the *Manduca sexta* BT-R$_1$ protein provided in FIG. 1. In general, naturally occurring allelic variants of *Manduca sexta* BT-R$_1$ will share significant homology, at least 75%, and generally at least 90%, to the BT-R$_1$ amino acid sequence provided in Seq. ID No:2. Allelic variants, though possessing a slightly different amino acid sequence than Seq. ID No:2, will be expressed as a transmembrane protein in the digestive tract of an insect or other organism. Typically, allelic variants of the BT-R$_1$ protein will contain conservative amino acid substitutions from the BT-R$_1$ sequence herein described or will contain a substitution of an amino acid from a corresponding position in a BT-R$_1$ homologue (a BT-R$_1$ protein isolated from an organism other than *Manduca sexta*).

One class of BT-R$_1$ allelic variants will be proteins that share a high degree of homology with at least a small region of the amino acid sequence provided in Seq. ID No:2, but may further contain a radical departure from the sequence, such as a non-conservative substitution, truncation, insertion or frame shift. Such alleles are termed mutant alleles of BT-R$_1$ and represent proteins that typically do not perform the same biological functions as does the BT-R$_1$ variant of Seq. ID No:2.

The BT-R$_1$ proteins of the present invention are preferably in isolated form. As used herein, a protein is said to be isolated when physical, mechanical or chemical methods are employed to remove the BT-R$_1$ protein from cellular constituents that are normally associated with the protein. A skilled artisan can readily employ standard purification methods to obtain an isolated BT-R$_1$ protein. The nature and degree of isolation will depend on the intended use.

The cloning of the BT-R$_1$ encoding nucleic acid molecule makes it possible to generate defined fragments of the BT-R$_1$ proteins of the present invention. As discussed below, fragments of BT-R$_1$ are particularly useful in: generating domain specific antibodies; identifying agents that bind to toxin binding domain on BT-R$_1$; identifying toxin-binding structures; identifying cellular factors that bind to BT-R$_1$; isolating homologues or other allelic forms of BT-R$_1$; and studying the mode of action of BT-toxins.

Fragments of the BT-R$_1$ proteins can be generated using standard peptide synthesis technology and the amino acid sequence of *Manduca sexta* BT-R$_1$ disclosed herein. Alternatively, as illustrated in Example 5, recombinant methods can be used to generate nucleic acid molecules that encode a fragment of the BT-R$_1$ protein. Fragments of the BT-R$_1$ protein subunits that contain particularly interesting structures can be identified using art-known methods such as by using an immunogenicity plot, Chou-Fasman plot, Garnier-Robson plot, Kyte-Doolittle plot, Eisenberg plot, Karplus-Schultz plot or Jameson-Wolf plot of the BT-R$_1$ protein. Fragments containing such residues are particularly useful in generating domain specific anti-BT-R$_1$ antibodies or in identifying cellular factors that bind to BT-R$_1$. One particular fragment that is preferred for use in identifying insecticidal agents is a soluble fragment of BT-R$_1$ that can bind to a member of the BT family of toxins. In Example 5, a fragment of BT-R$_1$ that binds to a BT-toxin is disclosed.

As described below, members of the BT-R$_1$ family of proteins can be used for, but are not limited to: 1) a target to identify agents that bind to BT-R$_1$, 2) a target or bait to identify and isolate binding partners and cellular factors that bind to BT-R$_1$, 3) an assay target to identify BT-R$_1$ and other receptor-mediated activity, and 4) a marker of cells that express a member of the BT-R$_1$ family of proteins.

B. Anti-BT-R$_1$ Antibodies

The present invention further provides antibodies that bind BT-R$_1$. The most preferred antibodies will selectively bind to BT-R$_1$ and will not bind (or will only bind weakly) to non-BT-R$_1$ proteins. Anti- BT-R$_1$ antibodies that are especially contemplated include monoclonal and polyclonal antibodies as well as fragments containing the antigen binding domain and/or one or more complement determining regions (CDRs) of these antibodies.

Antibodies are generally prepared by immunizing a suitable mammalian host using a BT-R$_1$ protein (synthetic or isolated), or fragment, in isolated or immunoconjugated form (Harlow, Antibodies, Cold Spring Harbor Press, NY (1989)). Regions of the BT-R$_1$ protein that show immunogenic structure can readily be identified using art-known methods. Other important regions and domains can readily be identified using protein analytical and comparative methods known in the art, such as Chou-Fasman, Garnier-Robson, Kyte-Doolittle, Eisenberg, Karplus-Schultz or Jameson-Wolf analysis. Fragments containing these residues are particularly suited in generating specific classes of anti-BT-R$_1$ antibodies. Particularly useful fragments include, but are not limited to, the BT-toxin binding domain of BT-R$_1$ identified in Example 5.

Methods for preparing a protein for use as an immunogen and for preparing immunogenic conjugates of a protein with a carrier such as BSA, KLH, or other carrier proteins are well known in the art. In some circumstances, direct conjugation with reagents such as carbodiimide may be used; in other instances linking reagents like those supplied by Pierce Chemical Co., Rockford, Ill., may be effective.

Administration of a BT-R$_1$ immunogen is conducted generally by injection over a suitable time period in combination with a suitable adjuvant, as is generally understood in the art. During the immunization schedule, titers of antibodies can be taken to determine adequacy of antibody formation.

Although the polyclonal antisera produced in this way may be satisfactory for some applications, for many other applications, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the $BT-R_1$ protein or $BT-R_1$ fragment. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of $F(ab')_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of the $BT-R_1$ protein can also be produced in the context of chimeric or CDR grafted antibodies of multiple species origin.

As described below, anti-$BT-R_1$ antibodies are useful as modulators of $BT-R_1$ activity, are useful in in vitro and in vivo antibody based assays methods for detecting $BT-R_1$ expression/activity, in generating toxin conjugates, for purifying homologues of *Manduca sexta* $BT-R_1$, in generating anti-ideotypic antibodies that mimic the $BT-R_1$ protein and in identifying competitive inhibitors of $BT$-toxin/$BT-R_1$ interactions.

C. $BT-R_1$ Encoding Nucleic Acid Molecules

As described above, the present invention is based, in part, on isolating nucleic acid molecules from *Manduca sexta* that encode $BT-R_1$. Accordingly, the present invention further provides nucleic acid molecules that encode the $BT-R_1$ protein, as herein defined, preferably in isolated form. For convenience, all $BT-R_1$ encoding nucleic acid molecules will be referred to as $BT-R_1$ encoding nucleic acid molecules, the $BT-R_1$ genes, or $BT-R_1$. The nucleotide sequence of the *Manduca sexta* nucleic acid molecule that encodes one allelic form of $BT-R_1$ is provided in FIG. 1.

As used herein, a "nucleic acid molecule" is defined as an RNA or DNA molecule that encodes a peptide as defined above, or is complementary to a nucleic acid sequence encoding such peptides. Particularly preferred nucleic acid molecules will have a nucleotide sequence identical to or complementary to the *Manduca sexta* DNA sequences herein disclosed. Specifically contemplated are genomic DNA, cDNAs, synthetically prepared DNAs, and antisense molecules, as well as nucleic acids based on an alternative backbone or including alternative bases, whether derived from natural sources or synthesized. A skilled artisan can readily obtain these classes of nucleic acid molecules using the herein described $BT-R_1$ sequences. However, such nucleic acid molecules, are defined fiber as being novel and unobvious over any prior art nucleic acid molecules encoding non-$BT-R_1$ proteins. For example, the $BT-R_1$ sequences of the present invention specifically excludes previously identified nucleic acid molecules that share only partial homology to $BT-R_1$. Such excluded sequences include identified members of the cadhedrin family of proteins.

As used herein, a nucleic acid molecule is said to be "isolated" when the nucleic acid molecule is substantially separated from contaminant nucleic acid molecules that encode polypeptides other than $BT-R_1$. A skilled artisan can readily employ nucleic acid isolation procedures to obtain an isolated $BT-R_1$ encoding nucleic acid molecule.

The present invention further provides fragments of the $BT-R_1$ encoding nucleic acid molecules of the present invention. As used herein, a fragment of a $BT-R_1$ encoding nucleic acid molecule refers to a small portion of the entire $BT-R_1$ sequence. The size of the fragment will be determined by its intended use. For example, if the fragment is chosen so as to encode the toxin binding domain of $BT-R_1$ identified in Example 5, then the fragment will need to be large enough to encode the toxin binding domain of the $BT-R_1$ protein. If the fragment is to be used as a nucleic acid probe or PCR primer, then the fragment length is chosen so as to obtain a relatively small number of false positives during probing/priming. Fragments of the *Manduca sexta* $BT-R_1$ gene that are particularly useful as selective hybridization probes or PCR primers can be readily identified from the entire $BT-R_1$ sequence using art-known methods.

Another class of fragments of $BT-R_1$ encoding nucleic acid molecules are the expression control sequence found upstream and downstream from the $BT-R_1$ encoding region found in genomic clones of the $BT-R_1$ gene. Specifically, tissue and developmental specific expression control elements can be identified as being 5' to the $BT-R_1$ encoding region found in genomic clones of the $BT-R_1$ gene. Such expression control sequence are useful in generating expression vectors for expressing genes in the digestive tract of a transgenic organism. As described in more detail below, a skilled artisan can readily use the $BT-R_1$ cDNA sequence herein described to isolate and identify genomic $BT-R_1$ sequences and the expression control elements found in the $BT-R_1$ gene.

Fragments of the $BT-R_1$ encoding nucleic acid molecules of the present invention (i.e., synthetic oligonucleotides) that are used as probes or specific primers for the polymerase chain reaction (PCR), or to synthesize gene sequences encoding $BT-R_1$ proteins, can easily be synthesized by chemical techniques, for example, the phosphotriester method of Matteucci, et al., *J Am Chem Soc* (1981) 103:3185–3191, or using automated synthesis methods. In addition, larger DNA segments can readily be prepared by well known methods, such as synthesis of a group of oligonucleotides that define various modular segments of the $BT-R_1$ gene, followed by ligation of oligonucleotides to build the complete modified $BT-R_1$ gene.

The $BT-R_1$ encoding nucleic acid molecules of the present invention may further be modified so as to contain a detectable label for diagnostic and probe purposes. As described above, such probes can be used to identify nucleic acid molecules encoding other allelic variants or homologues of the $BT-R_1$ proteins and as described below, such probes can be used to identify the presence of a $BT-R_1$ protein as a means for identifying cells that express a $BT-R_1$ protein. A variety of such labels are known in the art and can readily be employed with the $BT-R_1$ encoding molecules herein described. Suitable labels include, but are not limited to, biotin, radiolabeled nucleotides, biotin, and the like. A skilled artisan can employ any of the art-known labels to obtain a labeled $BT-R_1$ encoding nucleic acid molecule.

D. Isolation of Other BT-R$_1$ Encoding Nucleic Acid Molecules

The identification of the BT-R$_1$ protein from *Manduca sexta* and the corresponding encoding nucleic acid molecules, has made possible the identification of and isolation of: 1) BT-R$_1$ proteins from organisms other than *Manduca sexta*, hereinafter referred to collectively as BT-R$_1$ homologues, 2) other allelic and mutant forms of the *Manduca sexta* BT-R$_1$ protein (described above), and 3) the corresponding genomic DNA that contains the BT-R$_1$ gene. The most preferred source of BT-R$_1$ homologues are insects, the most preferred being members of the Lepidopteran, Coleopteran and Dipteran orders of insects. Evidence of the existence of BT-R$_1$ homologues is provided in FIG. 7.

Essentially, a skilled artisan can readily use the amino acid sequence of the *Manduca sexta* BT-R$_1$ protein to generate antibody probes to screen expression libraries prepared from cells and organisms. Typically, polyclonal antiserum from mammals such as rabbits immunized with the purified protein (as described above) or monoclonal antibodies can be used to probe an expression library, prepared from a target organism, to obtain the appropriate coding sequence for a BT-R$_1$ homologue. The cloned cDNA sequence can be expressed as a fusion protein, expressed directly using its own control sequences, or expressed by constructing an expression cassette using control sequences appropriate to the particular host used for expression of the enzyme.

Alternatively, a portion of the BT-R$_1$ encoding sequence herein described can be synthesized and used as a probe to retrieve DNA encoding a member of the BT-R$_1$ family of proteins from organisms other than *Manduca sexta*, allelic variants of the *Manduca sexta* BT-R$_1$ protein herein described, and genomic sequence containing the BT-R$_1$ gene. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively amplify/clone a BT-R$_1$-encoding nucleic acid molecule, or fragment thereof. A PCR denature/anneal/extend cycle for using such PCR primers is well known in the art and can readily be adapted for use in isolating other BT-R$_1$ encoding nucleic acid molecules. Regions of the *Manduca sexta* BT-R$_1$ gene that are particularly well suited for use as a probe or as primers can be readily identified by one skilled in the art.

Non-*Manduca sexta* homologues of BT-R$_1$, naturally occurring allelic variants of the *Manduca sexta* BT-R$_1$ gene and genomic BT-R$_1$ sequences will share a high degree of homology to the *Manduca sexta* BT-R$_1$ sequence herein described. In general, such nucleic acid molecules will hybridize to the *Manduca sexta* BT-R$_1$ sequence under high stringency. Such sequences will typically contain at least 70% homology, preferably at least 80%, most preferably at least 90% homology to the *Manduca sexta* BT-R$_1$ sequence of Seq. ID No:1.

In general, nucleic acid molecules that encode homologues of the *Manduca sexta* BT-R$_1$ protein will hybridize to the *Manduca sexta* BT-R$_1$ sequence under stringent conditions. "Stringent conditions" are those that (1) employ low ionic strength and high temperature for washing, for example, 0.015M NaCl/0.0015M sodium titrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

The presence of similar receptors in noninsect organisms as well as other insects besides those harboring BT-R$_1$ is supported by the sequence similarity of the BT-R$_1$ protein to that of the various members of the cadherin superfamily of proteins, which are membrane glycoproteins believed to mediate calcium-dependent cell aggregation and sorting. See, for example, Takeichi, M. *Science* (1991) 251:1451; and Takeichi, M. *N Rev Biochem* (1990) 59:237.

Included in this superfamily are desmoglien, desmocollins, the *Drosophila fat* tumor suppressor, *Manduca sexta* intestinal peptide transport protein and T-cadherin. All of these proteins share common extracellular motifs although their cytoplasmic domains differ. Goodwin, L. et al. *Biochem Biophys Res Commun* (1990) 173:1224; Holton, J. L. et al. *J Cell Sci* (1990) 97:239; Bestal, D. J. *J Cell Biol* (1992) 119:451; Mahoney, P. A. et al. *Cell* (1991) 853; Dantzig, A. H. et al. *Science* (1994) 264:430; and Sano, K. et al. *EMBO J* (1993) 12:2249. Inclusion of BT-R$_1$ in the cadherin superfamily is further supported by the report that EDTA decreases tile binding of CryIAb toxin of BT to the 210 kD receptor of *M. sexta* (Martinez-Ramirez, A. C. et al. *Biochm Biophys Res Commun* (1994) 201:782).

It is noted below that the amino acid sequence of BT-R$_1$ reveals that a calcium-binding motif is present. This is consistent with the possibility that cells having receptors to bind toxin may themselves survive although they render the tissues in which they are included permeable to solutes and thus effect disintegration of the tissue. Such a mechanism is proposed for the death of insects that ingest the toxin via the epithelial cells in their midgut by Knowles, B. H. et al. *Biochim Biophys Acta* (1987) 924:509. Such a mechanism is also supported in part by the results set forth in Example 4 hereinbelow which indicate that the effect of the toxin on embryonic 293 cells modified to express the receptor at their surface is reversible.

E. rDNA Molecules Containing a BT-R$_1$ Encoding Nucleic Acid Molecule

The present invention further provides recombinant DNA molecules (rDNAs) that contain a BT-R$_1$ encoding sequences as herein described, or a fragment thereof, such as a soluble fragment of BT-R$_1$ that contains the BT-toxin binding site. As used herein, a rDNA molecule is a DNA molecule that has been subjected to molecular manipulation in vitro. Methods for generating rDNA molecules are well known in the art, for example, see Sambrook et al., *Molecular Cloning* (1989). In the preferred rDNA molecules of the present invention, a BT-R$_1$ encoding DNA sequence that encodes a BT-R$_1$ protein or a fragment of BT-R$_1$, is operably linked to one or more expression control sequences and/or vector sequences.

The choice of vector and/or expression control sequences to which the BT-R$_1$ encoding sequence is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the BT-$R_1$ encoding sequence included in the rDNA molecule.

Expression control elements that are used for regulating the expression of an operably linked protein encoding sequence are known in the art and include, but are not limited to, inducible promoters, constitutive promoters, secretion signals, enhancers, transcription terminators and other regulatory elements. Preferably, an inducible promoter that is readily controlled, such as being responsive to a nutrient in the host cell's medium, is used. Further, for soluble fragments, it may be desirable to use secretion signals to direct the secretion of the BT-$R_1$ protein, or fragment, out of the cell.

In one embodiment, the vector containing a BT-$R_1$ encoding nucleic acid molecule will include a prokaryotic replicon, i.e., a DNA sequence having the ability to direct autonomous replication and maintenance of the recombinant DNA molecule intrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or viral promoter capable of directing the expression (transcription and transzlation) of the BT-$R_1$ encoding sequence in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories (Richmond, Calif.), pPL and pKK223 available from Pharmacia, Piscataway, N.J.

Expression vectors compatible with eukaryotic cells, preferably those compatible with vertebrate cells, can also be used to variant rDNA molecules that contain a BT-$R_1$ encoding sequence. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. Southern et al., *J Mol Anal Genet* (1982)1:327–341. Alternatively, the selectable marker can be present on a separate plasmid, and the two vectors are introduced by cotransfection of the host cell, and selected by culturing in. the presence of the appropriate drug for the selectable marker.

F. Host Cells Containing an Exogenously Supplied BT-$R_1$ Encoding Nucleic Acid Molecule The present invention further provides host cells transformed with a nucleic acid molecule that encodes a BT-$R_1$ protein of the present invention, either the entire BT-$R_1$ protein or a fragment thereof. The host cell can be either prokaryotic or eukaryotic. Eukaryotic cells useful for expression of a BT-$R_1$ protein are not limited, so long as the cell line is compatible with cell culture methods and compatible with the propagation of the expression vector and expression of a BT-$R_1$ gene. Preferred eukaryotic host cells include, but are not limited to, yeast, insect and mammalian cells, the most preferred being cells that do not naturally express a BT-$R_1$ protein.

Any prokaryotic host can be used to express a BT-$R_1$-encoding rDNA molecule. The preferred prokaryotic host is *E. coli*.

Transformation of appropriate cell hosts with an rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc Acad Sci USA* (1972) 69:2110; and Maniatis et al., *Molecular Cloning, A Laboratory Manual*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol* (1973) 52:456; Wigler et al., *Proc Natl Acad Sci USA* (1979) 76:1373–76.

Successfully transformed cells, i.e., cells that contain an rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J Mol Biol* (1975) 98:503, or Berent et al., *Biotech* (1985) 3:208 or the proteins produced from the cell assayed via an immunological method.

G. Production of a BT-$R_1$ Protein Using an rDNA Molecule

The present invention further provides methods for producing a BT-$R_1$ protein that uses one of the BT-$R_1$ encoding nucleic acid molecules herein described. In general terms, the production of a recombinant BT-$R_1$ protein typically involves the following steps.

First, a nucleic acid molecule is obtained that encodes a BT-$R_1$ protein or a fragment thereof, such as the nucleic acid molecule depicted in FIG. 1. The BT-$R_1$ encoding nucleic acid molecule is then preferably placed in an operable linkage with suitable control sequences, as described above, to generate an expression unit containing the BT-$R_1$ encoding sequence. The expression unit is used to transform a suitable host and the transformed host is cultured under conditions that allow the production of the BT-$R_1$ protein. Optionally the BT-$R_1$ protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in an appropriate host. The construction of expression vectors that are operable in a variety of hosts is accomplished using an appropriate combination of replicons and control sequences. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with BT-$R_1$ encoding sequences to produce a BT-$R_1$ protein.

H. Identification of Agents and Cellular Constituents that Bind to a BT-$R_1$ Protein Another embodiment of the present invention provides methods for identifying agents and cellular constituents that bind to BT-$R_1$. Specifically, agents and cellular constituents that bind to BT-$R_1$ can be identified by: 1) the ability of the agent/constituent to bind to BT-$R_1$, 2) the ability to block BT-toxin binding to BT-$R_1$, and/or 3) the ability to kill BT-$R_1$ expressing cells. Activity assays for BT-$R_1$ activity and binding and competitive assays using a BT-$R_1$ protein are suitable for use in high through-put screening methods, particularly using a soluble fragment of BT-$R_1$ that contains the BT-toxin binding domain. such as that disclosed in Example 5.

In detail, in one embodiment, BT-$R_1$ is mixed with an agent or cellular extract. After mixing under conditions that allow association of BT-$R_1$ with the agent or component of the extract, the mixture is analyzed to determine if the agent/component bound to the BT-$R_1$. Binding agents/components are identified as being able to bind to BT-$R_1$. Alternatively or consecutively, BT-$R_1$ activity can be directly assessed as a means for identifying agonists and antagonists of BT-$R_1$ activity.

Alternatively, targets that are bound by a BT-$R_1$ protein can be identified using a yeast two-hybrid system or using a binding-capture assay. In the yeast two hybrid system, an expression unit encoding a fusion protein made up of one subunit of a two subunit transcription factor and the BT-$R_1$ protein is introduced and expressed in a yeast cell. The cell is further modified to contain 1) an expression unit encoding a detectable marker whose expression requires the two subunit transcription factor for expression and 2) an expression unit that encodes a fusion protein made up of the second subunit of the transcription factor and a cloned segment of DNA. If the cloned segment of DNA encodes a protein that binds to the BT-$R_1$ protein, the expression results in the interaction of the BT-$R_1$ and the encoded protein. This brings the two subunits of the transcription factor into binding proximity, allowing reconstitution of the transcription factor. This results in the expression of the detectable marker. The yeast two hybrid system is particularly useful in screening a library of cDNA encoding segments for cellular binding partners of BT-$R_1$.

The BT-$R_1$ protein used in the above assays can be: an isolated and fully characterized protein, a fragment of a BT-$R_1$ protein (such as a soluble fragment containing the BT-toxin binding site), a cell that has been altered to express a BT-$R_1$ protein/fragment or a fraction of a cell that has been altered to express a BT-$R_1$ protein/fragment. Further, the BT-$R_1$ protein can be the entire BT-$R_1$ protein or a defined fragment of the BT-$R_1$ protein. It will be apparent to one of ordinary skill in the art that so long as the BT-$R_1$ protein or fragment can be assayed for agent binding, e.g., by a shift in molecular weight or activity, the present assay can be used.

The method used to identify whether an agent/cellular component binds to a BT-$R_1$ protein will be based primarily on the nature of the BT-$R_1$ protein used. For example, a gel retardation assay can be used to determine whether an agent binds to BT-$R_1$ or a fragment thereof. Alternatively, immunodetection and biochip technologies can be adopted for use with the BT-$R_1$ protein. A skilled artisan can readily employ numerous art-known techniques for determining whether a particular agent binds to a BT-$R_1$ protein.

Agents and cellular components can be further, or alternatively, tested for the ability to block the binding of a BT-toxin to a BT-$R_1$ protein/fragment. Alternatively, antibodies to the BT-toxin binding site or other agents that bind to the BT-toxin binding site on the BT-$R_1$ protein can be used in place of the BT-toxin.

Agents and cellular components can be further tested for the ability to modulate the activity of a BT-$R_1$ protein using a cell-free assay system or a cellular assay system. As the activities of the BT-$R_1$ protein become more defined, functional assays based on the identified activity can be employed.

As used herein, an agent is said to antagonize BT-$R_1$ activity when the agent reduces BT-$R_1$ activity. The preferred antagonist will selectively antagonize BT-$R_1$ not affecting any other cellular proteins. Further, the preferred antagonist will reduce BT-$R_1$ activity by more than 50%, more preferably by more than 90%, most preferably eliminating all BT-$R_1$ activity.

As used herein, an agent is said to agonize BT-$R_1$ activity when the agent increases BT-$R_1$ activity. The preferred agonist will selectively agonize BT-$R_1$ not affecting any other cellular proteins. Further, the preferred antagonist will increase BT-$R_1$ activity by more than 50%, more preferably by more than 90%, most preferably more than doubling BT-$R_1$ activity.

Agents that are assayed in the above method can be randomly selected or rationally selected or designed. As used herein, an agent is said to be randomly selected when the agent is chosen randomly without considering the specific sequences of the BT-$R_1$ protein or BT-toxin. An example of randomly selected agents is the use of a chemical library or a peptide combinatorial library, or a growth broth of an organism or plant extract.

As used herein, an agent is said to be rationally selected or designed when the agent is chosen on a nonrandom basis that takes into account the sequence of the target site and/or its conformation in connection with the agent's action. Agents can be rationally selected or rationally designed by utilizing the peptide sequences that make up the BT-$R_1$ protein and BT-toxin. For example, a rationally selected peptide agent can be a peptide whose amino acid sequence is identical to a fragment of a BT-$R_1$ protein or BT-toxin.

The agents tested in the methods of the present invention can be, as examples, peptides, small molecules, and vitamin derivatives, as well as carbohydrates. A skilled artisan can readily recognize that there is no limit as to the structural nature of the agents used in the present screening method. One class of agents of the present invention are peptide agents whose amino acid sequences are chosen based on the amino acid sequence of the BT-$R_1$ protein or BT-toxin. Small peptide agents can serve as competitive inhibitors of BT-$R_1$ protein activity.

Peptide agents can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of the $BT-R_1$ protein. As described above, antibodies are obtained by immunization of suitable mammalian subjects with peptides, containing as antigenic regions, those portions of the $BT-R_1$ protein intended to be targeted by the antibodies. Critical regions particularly include the BT-toxin binding domain identified in Example 5. Such agents can be used in competitive binding studies to identify second generation $BT-R_1$ binding agents.

The cellular extracts tested in the methods of the present invention can be, as examples, aqueous extracts of cells or tissues, organic extracts of cells or tissues or partially purified cellular fractions. A skilled artisan can readily recognize that there is no limit as to the source of the cellular extract used in the screening method of the present invention. The preferred source for isolating cellular binding partners of $BT-R_1$ are cells that express $BT-R_1$ or cells that are in close proximity to $BT-R_1$ expressing cells.

An outline of one screening method is as follows. Cells are modified by transfection, retroviral infection, electroporation or other known means, to express a $BT-R_1$ protein and then cultured under conditions wherein the receptor protein is produced and displayed. If desired, the cells are then recovered from the culture for use in the assay, or the culture itself can be used per se.

In the assays, the modified cells are contacted with the candidate toxin and the effect on metabolism or morphology is noted in the presence and absence of the candidate. The effect may be cytotoxic—i.e., the cells may themselves exhibit one of the indices of cell death, such as reduced thymidine uptake, slower increase in optical density of the culture, reduced exclusion of vital dyes (e.g., trypan blue), increased release of viability markers such as chromium and rubidium, and the like. The differential response between the toxin-treated cells and the cells absent the toxin is then noted. The strength of the toxin can be assessed by noting the strength of the response.

These assays may be conducted directly as described above or competitively with known toxins. For example, one approach might be to measure the diminution in binding of labeled BT cry toxin in the presence and absence of the toxin candidate.

In addition to simply screening candidates, the screen can be used to devise improved forms of toxins which are more specific or less specific to particular classes of insects as desired. The ability to determine binding affinity ($K_a$ and $K_d$), dissociation and association rates, and cytotoxic effects of a candidate allows quick, accurate and reproducible screening techniques for a large number of toxins and other ligands under identical conditions which was not possible heretofore. Such information will facilitate the selection of the most effective toxins and ligands for any given receptor obtained from any desired host cell.

Competition assays may also employ antibodies that are specifically immunoreactive with the receptor. Such antibodies can be prepared in the conventional manner by administering the purified receptor to a vertebrate animal, monitoring antibody titers and recovering the antisera or the antibody-producing cells for immortalization, to obtain immortalized cells capable of secreting antibodies of the appropriate specificity. Techniques for obtaining immortalized B cells and for screening them for secretion of the desired antibody are now conventional in the art. The resulting monoclonal antibodies may be more effective than the polyclonal antisera as competition reagents; furthermore, the availability of the immortalized cell line secreting the desired antibody assures uniformity of production of the same reagent over time. The information and the structural characteristics of toxins and ligands tested will permit a rational approach to designing more efficient toxins and ligands. Additionally, such assays will lead to a better understanding of the function and the structure/function relationship of both toxin/ligand and $BT-R_1$ analogs. In turn, this will allow the development of highly effective toxins/ligands. Ligands include natural and modified toxins, antibodies (anti-receptor and antiidiotypic antibodies which mimic a portion of a toxin that binds to a receptor, and whatever small molecules bind the receptors.

I. Uses of Agents that Bind to a $BT-R_1$ Protein

As provided in the Background section, $BT-R_1$ is the target for the insecticidal activity of BT-toxins. Agents that bind a $BT-R_1$ protein can be used: 1) to kill $BT-R_1$ expressing cells, 2) to identify agents that block the interaction of a BT-toxin with $BT-R_1$ and 3) in methods for identifying cells that express $BT-R_1$.

The methods employed in using the $BT-R_1$ binding agents will be based primarily on the nature of the $BT-R_1$ binding agent and its intended use. For example, a $BT-R_1$ binding agent can be used to: deliver a conjugated toxin to a $BT-R_1$ expressing cell; modulate $BT-R_1$ activity; directly kill $BT-R_1$ expressing cells; or screen for and identify competitive binding agents. An agent that inhibits the activity of $BT-R_1$ can be used to directly inhibit the growth of $BT-R_1$ expressing cells. Further, identified cellular factors that bind to $BT-R_1$ can, themselves, be used in binding/competitive assays to identify agonist and antagonists of $BT-R_1$.

J. Methods for Identifying the Presence of a $BT-R_1$ Protein or Gene

The present invention further provides methods for identifying cells, tissues or organisms expressing a $BT-R_1$ protein or a $BT-R_1$ gene. Such methods can be used to diagnose the presence of cells or an organism that expresses a $BT-R_1$ protein in vivo or in vitro. The methods of the present invention are particularly useful in the determining the presence of cells that are a target for BT-toxin activity or for identifying susceptibility of an organism to a BT-toxin or BT-toxin-like agent. Specifically, the presence of a $BT-R_1$ protein can be identified by determining whether a $BT-R_1$ protein, or nucleic acid encoding a $BT-R_1$ protein, is expressed in a cell, tissue or organism.

A variety of immunological and molecular genetic techniques can be used to determine if a $BT-R_1$ protein is expressed/produced in a particular cell or sample. In general, an extract containing nucleic acid molecules or an extract containing proteins is prepared. The extract is then assayed to determine whether a $BT-R_1$ protein, or a $BT-R_1$ encoding nucleic acid molecule, is produced in the cell.

For example, to perform a diagnostic test based on nucleic acid molecules, a suitable nucleic acid sample is obtained and prepared using conventional techniques. DNA can be prepared, for example, simply by boiling a sample in SDS. The extracted nucleic acid can then be subjected to amplification, for example by using the polymerase chain reaction (PCR) according to standard procedures, such as a RT-PCR method, to selectively amplify a $BT-R_1$ encoding nucleic acid molecule or fragment thereof The size or presence of a specific amplified fragment (typically following restriction endonuclease digestion) is then determined using gel electrophoresis or the nucleotide sequence of the fragment is determined (for example, see Weber and May *Am J Hum Genet* (1989) 44:388–339; Davies, J. et al. *Nature* (1994) 371:130–136)). The resulting size of the fragment or sequence is then compared to the known BT-R$_1$ proteins encoding sequences, for example via hybridization probe. Using this method, the presence of a BT-R$_1$ protein can be identified.

To perform a diagnostic test based on proteins, a suitable protein sample is obtained and prepared using conventional techniques. Protein samples can be prepared, for example, simply by mixing a sample with SDS followed by salt precipitation of a protein fraction. The extracted protein can then be analyzed to determine the presence of a BT-R$_1$ protein using known methods. For example, the presence of specific sized or charged variants of a protein can be identified using mobility in an electric filed. Alternatively, antibodies can be used for detection purposes. A skilled artisan can readily adapt known protein analytical methods to determine if a sample contains a BT-R$_1$ protein.

Alternatively, BT-R$_1$ protein or gene expression can also be used in methods to identify agents that decrease the level of expression of a BT-R$_1$ gene. For example, cells or tissues expressing a BT-R$_1$ protein can be contacted with a test agent to determine the effects of the agent on BT-R$_1$ protein/ gene expression. Agents that activate BT-R$_1$ protein/gene expression can be used as an agonist of BT-R$_1$ activity whereas agents that decrease BT-R$_1$ protein/gene expression can be used as an antagonist of BT-R$_1$ activity.

K. Methods to Sensitize Cells

The present invention further provides methods of sensitizing cells such that they become susceptible to killing with a BT-toxin, or a BT-toxin analog. Specifically, host cells transformed to express BT-R$_1$ receptor, or a homolog of the BT-R$_1$ receptor, become sensitive to the mode of action of BT-toxins. The binding of a BT-toxin to a BT-R$_1$ receptor expressed on the surface of the transformed tells results in induction of a cellular death and apoptosis of the cell expressing the BT-R$_1$ receptor. Accordingly, the BT-R$_1$ receptor is an appropriate candidate for use in transforming cells in which it is desirable to induce cell death.

There are numerous situations in which it is desirable to introduce the selected gene into a selected population of cells, thus bringing about cell death. One such example is in the therapeutic treatment of cancer cells. In using specifically targeted vectors for delivery of BT-R$_1$-encoding DNA molecules into a tumor cell, tumor cells within a patient can be engineered to express a BT-R$_1$ protein. Such cells then become susceptible to death upon treatment with a BT-toxin. Since BT-toxin is not normally toxic to mammalian cells, this method is particularly applicable to inducing cell death in particular cells in a mammalian host. Other situations where it may be desirable to stimulate cell death in particular cells or cell lines are in the treatment of autoimmune disorders and in the treatment of cells harboring pathogens, such as malaria or HIV agents.

The choice of the actual steps employed to introduce a BT-R$_1$-encoding DNA molecule into a cell to render the cells susceptible to treatment with BT-toxin is based primarily on the cell type that is to be altered, the conditions under which the cell type will be altered, and the overall use envisioned. A skilled artisan can readily adapt art-known methods for use with the BT-R$_1$-encoding DNA molecule of the present invention.

L. Animal Models and Gene Therapy

The BT-R$_1$ gene and the BT-R$_1$ protein can also serve as a target for generating transgenic organisms in which the pattern of BT-R$_1$ expression has been altered. For example, in one application, BT-R$_1$ deficient insects or insect cells can be generated using standard knock-out procedures to inactivate a BT-R$_1$ gene, or, if such animals are non-viable, inducible BT-R$_1$ antisense molecules can be used to regulate BT-R$_1$ activity/expression. Alternatively, cells or an organism can be altered so as to contain a *Manduca sexta* BT-R$_1$ encoding nucleic acid molecule or an antisense-BT-R$_1$ expression unit that directs the expression of a BT-R$_1$ protein or an antisense molecule in a tissue specific fashion. In such uses, an organism or cells, for example insects or insect cells, is generated in which the expression of a BT-R$_1$ gene is altered by inactivation or activation and/or replaced by a *Manduca sexta* BT-R$_1$ gene. This can be accomplished using a variety of art-known procedures such as targeted recombination. Once generated, the BT-R$_1$ expression altered cells or organisms can be used to 1) identify biological and pathological processes mediated by the BT-R$_1$ protein, 2) identify proteins and other genes that interact with the BT-R$_1$ protein, 3) identify agents that can be exogenously supplied to overcome a BT-R$_1$ protein deficiency and 4) serve as an appropriate screen for identifying mutations within the BT-R$_1$ gene that increases or decreases activity. For example, it is possible to generate transgenic insects, such as members of the dipteran order, expressing the *Manduca sexta* minigene encoding BT-R$_1$ in a tissue specific-fashion and test the effect of over-expression of the protein in tissues and cells that normally do not contain the BT-R$_1$ protein.

M. Use of Expression Control Elements of the BT-R$_1$ Gene

The present invention further provides the expression control sequences found 5' of the of the newly identified BT-R$_1$ gene in a form that can be used in generating expression vectors. Specifically, the BT-R$_1$ expression control elements, such as the BT-R$_1$ promoter, that can readily be identified as being 5' from the ATG start codon in the BT-R$_1$ gene, can be used to direct the expression of an operably linked protein encoding DNA sequence. Since BT-R$_1$ expression is mostly tissue-specific, the expression control elements are particularly useful in directing the expression of an introduced transgene in a tissue specific fashion. A skilled artisan can readily use the BT-R$_1$ gene promoter and other regulatory elements to generate expression vectors using methods known in the art.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLE 1

Purification and Sequence Determination of BT-R$_1$ Protein

Midguts of *M. sexta* were extracted and the BT-R$_1$ protein purified according to the method of Vadlamudi, R. K. et al. *J Biol Chem* (1993) 268:1233, referenced above and incorporated herein by reference. The electroeluted band was confirmed to contain BT-R$_1$ protein by binding to $^{125}$I-cryIAb toxin. In gel electrophoresis, the protein bound to toxin had an apparent weight of approximately 210 kD under reducing and nonreducing conditions.

The purified electroeluted BT-R$_1$ was subjected to cyanogen bromide digestion and the cyanogen bromide fragments separated on a 17% high-resolution tricine SDS-polyacrylamide gel as described by Schagger, H. et al. *Anal Biochem* (1987) 166:368. The separated fragments were transferred to Problott membranes (Applied Biosystems) and five bands were extracted and subjected to microsequencing using standard instrumentation. The amino acid sequences obtained were:

1. (Met)-Leu-Asp-Tyr-Glu-Val-Pro-Glu-Phe-Gln-Ser-Ile-Thr-Ile-Arg-Val-Val-Ala-Thr-Asp-Asn-Asn-Asp-Thr-Arg-His-Val-Gly-Val-Ala (SEQ ID NO:3);
2. (Met)-X-Glu-Thr-Tyr-Glu-Leu-Ile-Ile-His-Pro-Phe-Asn-Tyr-Tyr-Ala (SEQ ID NO:4);
3. (Met)-X-X-X-His-Gln-Leu-Pro-Leu-Ala-Gln-Asp-Ile-Lys-Asn-His (SEQ ID NO:5);
4. (Met)-Phe/Pro-Asn/Ile-Val-Arg/Tyr-Val-Asp-Ile/Gly (SEQ ID NO:6);
5. (Met)-Asn-Phe-Phe/His-Ser-Val-Asn-Arg/Asp-Glu (SEQ ID NO:7).

EXAMPLE 2

Recovery of cDNA

An *M. sexta* cDNA library was constructed from midgut tissue in λgt10 using the Superscript Choice System according to the manufacturer's instructions (Life Technologies, Inc.). Degenerate oligonucleotide probes were constructed based on the peptide sequences determined in Example 1 using the methods and approach described in Zhang, S. et al. *Gene* (1991) 105:61. Synthetic oligonucleotides corresponding to peptides 1–3 of Example 1 were labeled with $\alpha^{32}P$ using polynucleotide kinase and used as probes as described in the standard cloning manual of Maniatis, T. et al. *Molecular Cloning: A Laboratory Manual* (Cold Spring Harbor Laboratory, Cold Spring Harbor, N.Y., 2nd ed. 1989). A clone hybridizing to all three probes identified from 40 positive clones as hybridizing to all three of the probes was plaque-purified from a screen of $4 \times 10^5$ recombinants and subcloned into pBluescript (Stratagene). It contained an insert of 5571 bp.

Double-stranded cDNA in pBluescript was sequenced in both directions by the dideoxy termination method with Sequanase (USB) according to the manufacturer's instructions. The sequencing showed an open reading frame of 4584 base pairs or 1528 amino acids along with a polyadenylation signal at position 5561. The sequence obtained and the deduced amino acid sequence is shown in FIG. 1.

Thus, the deduced protein has a molecular mass of 172 kD and a pI of approximately 4.5. The amino acid sequences of the cyanogen bromide fragments of native receptor match perfectly within the deduced amino acid sequence. The open reading frame begins with an ATG that is flanked by the consensus translation initiation sequence GAGATGG for eucaryotic mRNAs as described by Kozak, M. *Nucleic Acids Res* (1987) 15:8125.

Figure 2I:
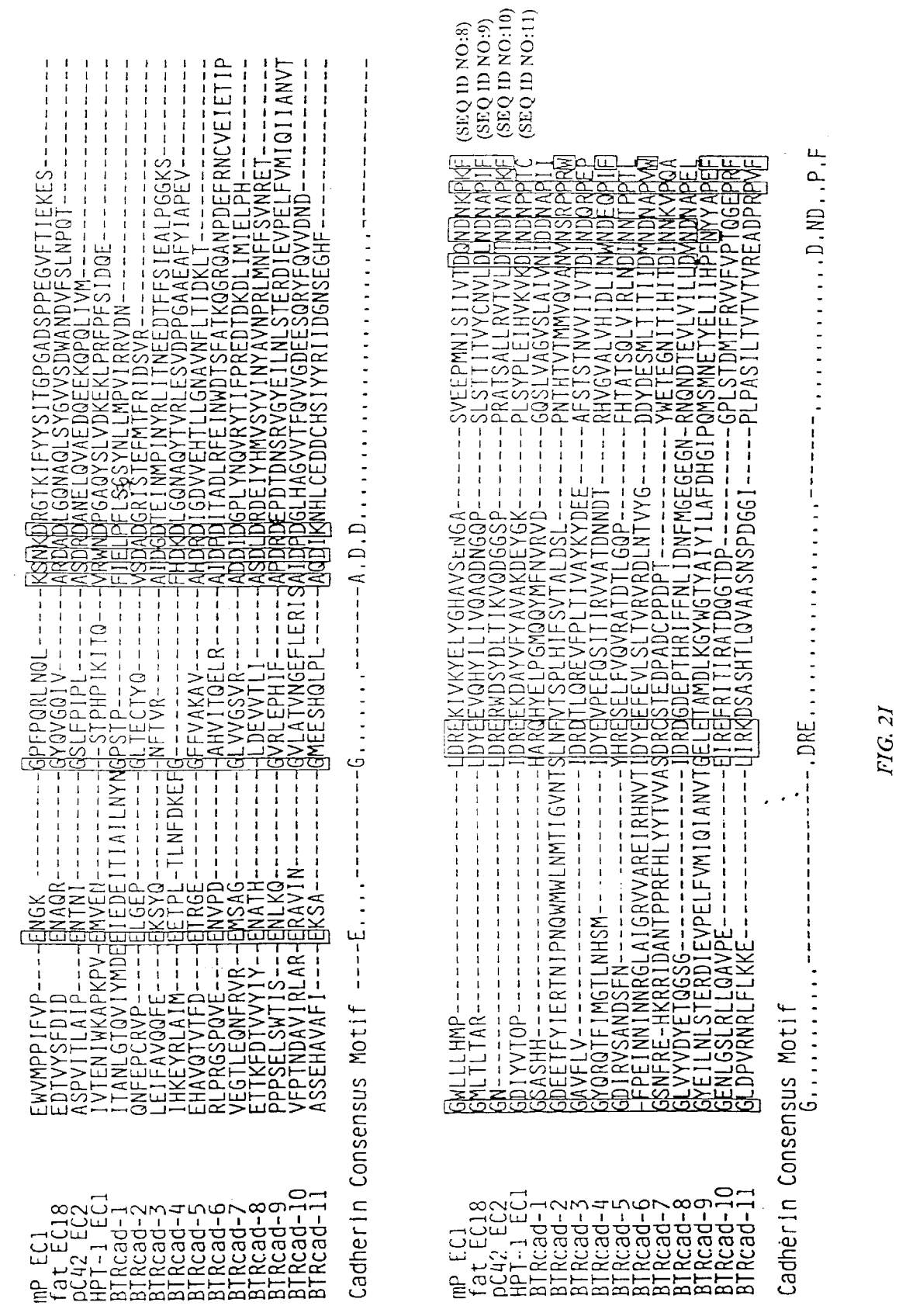

As shown in FIGS. 2A–2H, the deduced amino acid sequence includes a putative signal, shown underlined, preceding the mature N-terminus Asn-Glu-Arg-etc. Eleven repeats (cad1–cad11) are shown in the extracellular region upstream of the membrane domain, shown with the heavy underline, at positions 1406–1427 (SEQ ID NO:2). The end of the 11th repeat is shown with an arrowhead. The positions of the five CNBR fragments are also shown under the complete sequence.

FIG. 2I compares the BT-R$_1$ sequence obtained herein SEQ ID NO:2) with other members of the cadherin family. Like known cadherins, the external domain of BT-R$_1$ is highly repetitive and contains 11 repeats (cad1–cad11; see FIG. 2I). The other cadherins compared in FIG. 2I are mouse P cadherin (mP EC1); *Drosophila fat* EC18 (fat EC18) and protocadherin (PC42 EC2), and *Manduca sexta* intestinal transporter (HPT-1-EC-1). The eleven repeats of the cadherin motif in BT-R$_1$ (cad1–cad11) are individually aligned with a single motif sequence from each of the other members of the cadherin family. Conserved residues are boxed. The greatest similarity of BT-R$_1$ to the cadherins is with the extracellular repeats of the cadherin motif of mouse P-cadherin, *Drosophila fat* tumor suppressor and the protocadherins, although homologies are not high (20–40 homology and 30–60 percent similarity). The conserved repeats of BT-R$_1$ included AXDXD (SEQ ID NO.12), DXE, DXNDXXP (SEQ ID NO:13), one glutamic acid residue and two glycine residues (FIG. 2I). Motifs A/VXDXD (SEQ ID NO:14), DXNDN (SEQ ID NO:15) are the consensus sequences for calcium binding and two such regions are present in a typical cadherin repeat. In all repeats of BT-R$_1$ the sequence DXNDN (SEQ ID NO:15) is preceded by 8 to 14 hydrophobic amino acids. Similar hydrophobic sequences also have been observed in the cadherins. The length of the hydrophobic stretches suggests that these areas are not transmembrane regions buy that the represent J-sheet structures commonly present in cadherin-like repeats. BT-R$_1$ contains a putative cytoplasmic domain of 101 amino acids, smaller than vertebrate cadherin cytoplasmic domains (160 amino acids), and shows no homology to any of the cadherin cytoplasmic domains or to cytoplasmic domains of other proteins to, which it has been compared in a current sequence data base.

To confirm that the sequenced clone encoded full-length BT-R$_1$ protein, total mRNA was prepared from midguts of *M. sexta* subjected to Northern blot by hybridization with the antisense 4.8 kb Sacd fragment of the BT-R$_1$ cDNA clone. The Northern blot analysis was conducted by hybridizing to the antisense probe at 42° C. and 50% formamide, 5×Denhardt's Reagent, 5×SSCP and 50 μg/ml salmon sperm DNA. The filter was then washed two times with 1×SSC+0.1% SDS and two times with 0.15×SSC+0.1% SDS at 42° C. Each wash was roughly 20 minutes. The filter was then exposed to X-ray film for 24 hours. The 4.8 kb probe hybridized to a single 5.6 kb band.

The BT-R$_1$ clone was translated using rabbit reticulolysate and the resulting translated products were immunoprecipitated with antisera raised against native protein encoded by BT-R$_1$. For the in vitro translation, pBluescript plasmid containing BT-R$_1$ cDNA was linearized and transcribed with T$_3$ polymerase (Pharmacia). The translation was conducted according to manufacturer's instructions with nuclease-treated rabbit reticulolysate (Life Technologies, Inc.). After one hour of incubation at 30° C., the reaction mixture was combined with an equal volume of SDS buffer or lysed with 50 mM Tris buffer containing 1% NP40 and 250 mM NaCl (pH 8.0) for immunoprecipitation. Preimmune serum was used as a control. Translation and immunoprecipitation products were electrophoresed on a 7.5% SDS-polyacrylamide gel fixed, treated with Enhance (Dupont NEN), dried and exposed to X-ray film for 12 hours.

Two protein bands of approximately 172 kD and 150 kD as determined by SDS-PAGE were obtained; it is postulated that the 150 kD translation product was due to initiation of translation from an internal methionine at amino acid 242. This is consistent with the observations of Kozak, M. *Mol Cell Biol* (1989) 9:5073.

Thus, both results confirm that a full-length clone was obtained.

EXAMPLE 3

Recombinant Production and Characteristics of the BT-R$_1$ Protein

The BT-R$_1$ cDNA clone was subcloned into the mammalian expression vector pcDNA3 (Invitrogen) and the construct transfected into COS-7 cells. Membranes isolated from the COS-7 transfectants were solubilized, electrophoresed and ligand blotted with $^{125}I$-CryIAb toxin. The cells were harvested 60 hours after transfection, washed with phosphate-buffered saline and lysed by freezing in liquid nitrogen. Cell membranes were prepared by differential centrifugation as described by Elshourbagy, N.A. et al. *J Biol Chem* (1993) 266:3873. Control cells were COS-7 cells transfected with pcDNA3.

The cell membranes (10 μg) were separated on 7.5% SDS-PAGE blotted to a nylon membrane and blocked with Tris-buffered saline containing 5% nonfat dry milk powder, 5% glycerol and 1% Tween-20. The nylon membrane was then incubated with $^{125}I$-CryIAb toxin ($2\times10^5$ cpm/ml) for two hours with blocking buffer, dried and exposed to X-ray film at −70° C. The labeled toxin bound to a 210±5 kD protein; the 210 kD band was observed only in lanes containing membranes prepared from either *M. sexta* or COS-7 cells transfected with the BT-R$_1$ cDNA construct containing 4810 bp of cDNA comprising the open reading frame.

The discrepancy between the 210 kD protein expressed and the calculated 172 kD molecular weight is due to glycosylation of the protein; in vitro translation of the cDNA clone, as described above, which does not result in glycosylation, does produce the 172 kD protein. To verify this, the COS-7 produced protein was subjected to digestion with N-glycosidase-F by first denaturing the purified protein by boiling in 1% SDS for 5 minutes followed by addition of NP-40 to a final concentration of 1% in the presence of 0.1% SDS, and then incubating the denatured protein in sodium phosphate buffer, pH 8.5 at 37° C. with N-glycosidase-F for 10 hours. Controls were incubated under the same conditions without enzyme. Digestion products were separated on a 7.5% SDS-PAGE and stained with Coomassie brilliant blue. This glycosidase treatment reduced the molecular weight of BT-R$_1$ protein from 210 to 190 kD; this indicates N-glycosylation at some of the 16 consensus N-glycosylation sites in the protein. Treatment of BT-R$_1$ with O-glycosidase and neuraminidase did not alter the mobility of the protein.

In addition, embryonic 293 cells were transfected with the BT-R$_1$ cDNA clone in pcDNA3 and incubated with the labeled toxin (0.32 nM) in the presence of increasing concentrations (0 to $10^{-6}$ M) of unlabeled toxin. Nonspecific binding was measured as bound radioactivity in the presence of 1 TM unlabeled toxin. A value for the dissociation constant (K$_d$) of 1015 pM was determined by Scatchard analysis; this is approximately the same value that was obtained for the natural receptor as described by Vadlamudi, R. K. et al. *J Biol Chem* (1993) (supra).

EXAMPLE 4

Physiological Effect of BT Toxin on Modified Embryonic 293 Cells

Both unmodified embryonic 293 cells, and 293 cells which have been modified to produce the BT-R$_1$ receptor as described in Example 3, when cultured in vitro form adherent star-shaped clusters. When BT toxin (200 nM) is added to serum-free medium, the clusters round up and release from the plastic surfaces of the culture dish. This effect is also observed under known conditions of cytotoxicity for 293 cells. The foregoing effect is observed only when the cells are cultured in serum-free medium since the toxin binds to serum and would thus be ineffective under conditions where serum is present.

However, in the presence of anti-receptor antisera, this effect of BT toxin is blocked. Also, when serum is added back to a culture of modified E293 cells which has been treated in serum-free conditions with the toxin, the cells revert to their normal star-shaped adherent cluster shapes. This indicates that the effect of the toxin is reversible.

EXAMPLE 5

Identification of a Fragment of BT-R$_1$ that Binds to a BT Toxin

To understand some of the properties of BT-R$_1$, research has been undertaken to define the location of the BT-R$_1$/Cry1Ab protein-protein interaction. The full-length wild-type amino acid sequence of BT-R$_1$ is provided in FIG. 1 with a block diagram of a possible cadherin-like structure for BT-R$_1$ shown in FIG. 3. In both figures, restriction digest sites from the cDNA are provided relative to the positions at which they would disrupt the amino acid coding sequence.

Figure 4:
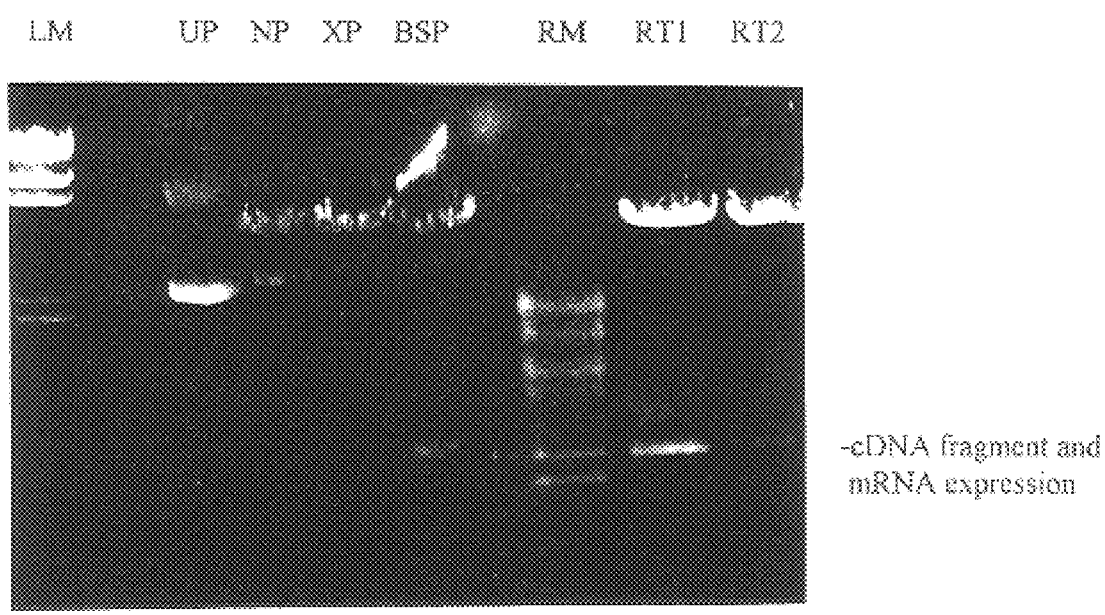
FIG. 4 shows the clone characterization of the BamHI-SacI fragment of BT-$R_1$. LM is HindIII cut Lambda marker; UP is the uncut plasmid clone; NP is NsiI cut plasmid; XP is XhoI cut plasmid; BSP is BamHI and SacI cut plasmid showing the cloned fragment from BT-$R_1$; RM is mRNA size marker; and RT1 and RT2 are transcribed mRNAs from the cloned BT-$R_1$ fragment.

A small fragment lying between the BamHI and Sacd restriction sites of wild-type BT-R$_1$ was cloned into the vector pCITE (Novagen). This vector contains transcription/translation sequences designed for use in a rabbit reticulocyte lysate (RRL) system. The clone has been analyzed by restriction mapping and mRNA expression (FIG. 4). Lane UP shows the uncut plasmid and lanes NP and XP show restriction digests using NsiI and XhoI, respectively. NsiI is used because it has only one restriction site lying within the Bam-Sac fragment and does not cut anywhere within the pCITE vector. The BSP lane shows the restriction digest of the clone using BamHI and SacI. The digest releases the cloned fragment which separates at about 700 base pairs. The RT1 and RT2 lanes show mRNA transcription from the clone after linearization with XhoI. The mRNA separates at the expected 1350 base pairs.

Figure 5:
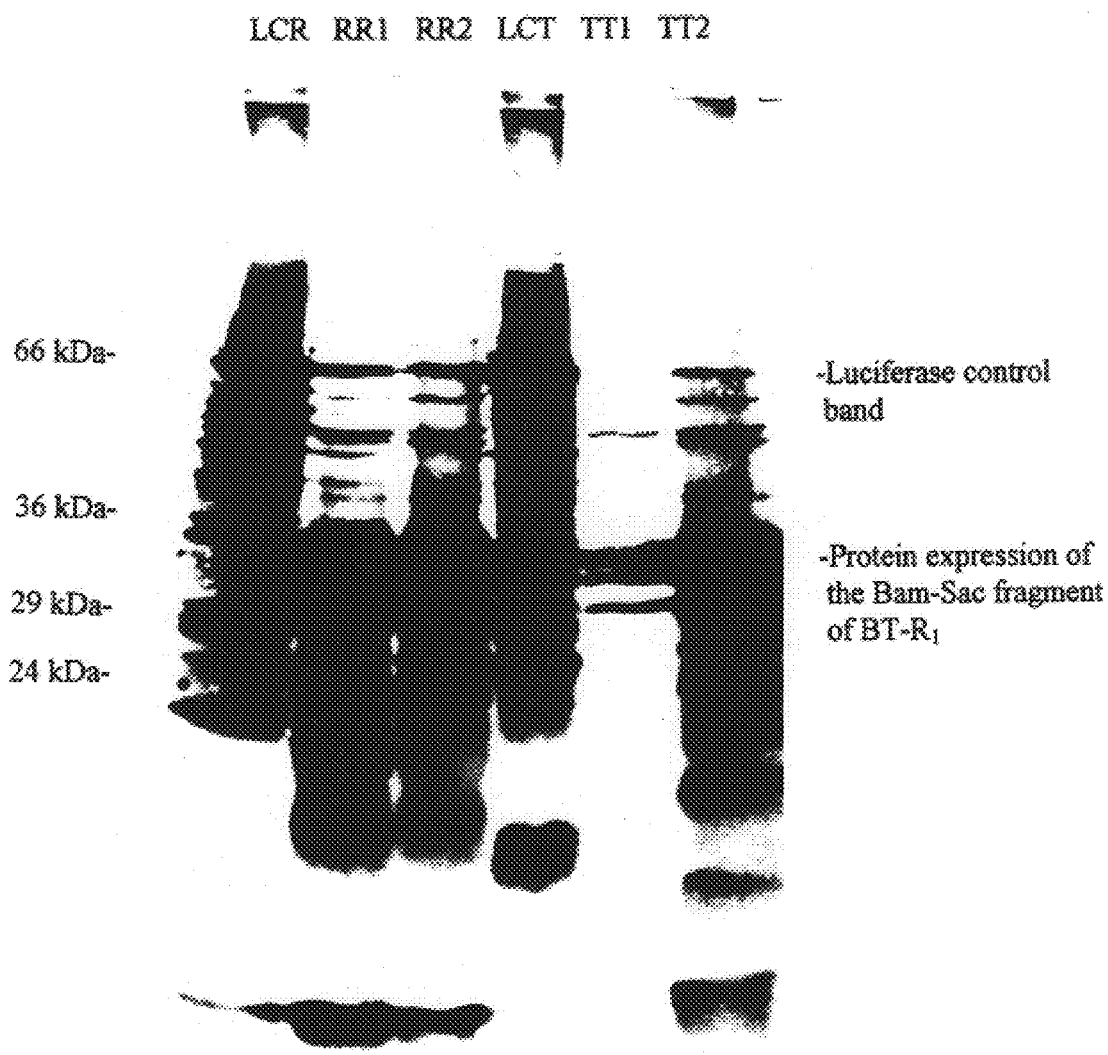
FIG. 5 illustrates the detection of protein expression from the plasmid containing the Bam-Sac fragment of BT-$R_1$ using $^{35}S$-methionine as a tag. LCR is a luciferase control mRNA to show that the rabbit reticulocyte lysates are functional; RR1 and RR2 are expression products of the Bam-Sac fragment of BT-$R_1$ produced in rabbit reticulocytes from mRNA; LCT is a luciferase control plasmid to show that the transcription/translation kit is functional; and TT1 and TT2 are expression products of the Bam-Sac fragment of BT-$R_1$ produced in a transcription/translation kit.

Protein for analysis has been prepared from this clone in two ways. First, an RRL translation kit was employed to produce protein from the mRNA transcription reaction described above. Second, the plasmid was added directly to an RRL based transcription and translation (TNT) coupled kit. Protein production was detected using $^{35}S$-methionine as a tag (FIG. 5). The LCR lane shows production of luciferase protein from mRNA in an RRL kit and the LCT lane is luciferase protein from a plasmid containing the luciferase coding sequence translated in the TNT kit. Both are positive controls to demonstrate that the two translation kits are operational. The major bands for luciferase translation are observed at 66 kDa. The lanes labeled as RR$_1$ and RR2 show expression of the polypeptide sequence of the Bam-Sac fragment of BT-R$_1$ translated from mRNA in the RRL kit. The lanes TT1 and TT2 are translations from the pCITE plasmid containing the Bam-Sac fragment from the TNT kit. All four lanes possess a major band at 30 kDa which is the expected size of the Bam-Sac fragment with the addition of a coded antibody tag called S-tag. S-tag is part of the multicloning site of pCITE.

Figure 6:
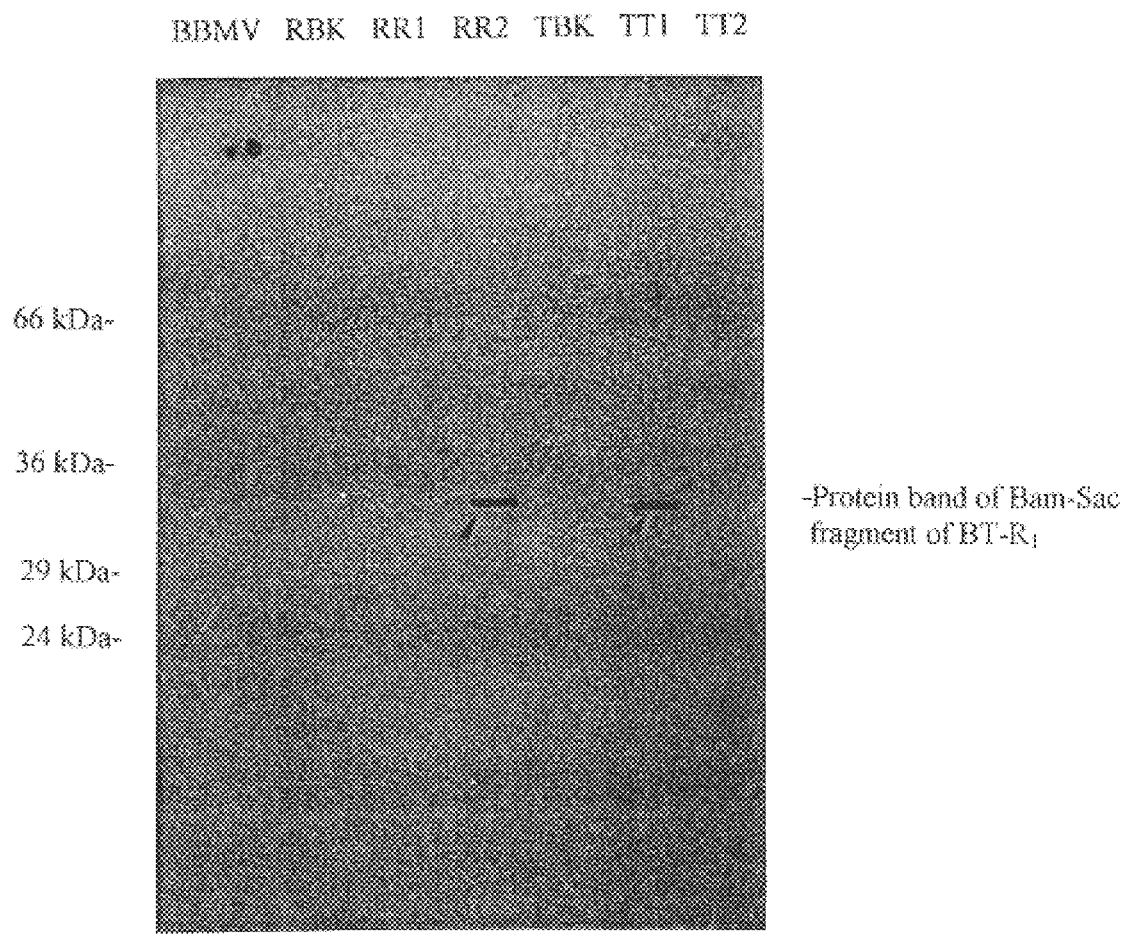
FIG. 6 shows a radio-blot of the Bam-Sac fragment of BT-$R_1$ with $^{125}I$-labeled CR1Ab. BBMV is the brush border membrane vesicles from the midgut of *M. sexta* containing the wild-type BT-$R_1$ receptor protein; RBK is a rabbit reticulocyte blank; RR1 and RR2 are the expression products of the Bam-Sac fragment of BT-$R_1$ produced in rabbit reticulocytes from mRNA; TBK is a transcription/translation kit blank; TT1 and TT2 are expression products of the Bam-Sac fragment of BT-$R_1$ produced in a transcription/translation kit. The arrows point to two of the bands.

The clone was then tested for its ability to bind the insecticidal toxin Cry1Ab. Polypeptide translation of the Bam-Sac fragment of BT-R$_1$ was carried out in duplicate as described above. The only change is that the $^{35}S$-methionine tag was left out of the reaction mixtures to produce non-radiolabeled proteins. The proteins were separated by SDS-PAGE, blotted to nitrocellulose and hybridized with $^{125}$I-labeled Cry1Ab (FIG. 6). BBMV is wild-type BT-R$_1$ prepared from the midgut brush border membrane vesicles (BBMV) of *M. sexta* and, is used as a positive control. RBK and TBK are RRL and TNT control reactions prepared without mRNA or plasmid present to determine whether proteins endogenous to either kit bind CR1Ab. R$_1$ and RR2 are translations from the RRL kit and TT1 and TT2 are from the TNT kit. A single 30-kDa band appears in each of these lanes. Two are marked by arrows. These bands demonstrate that the Bam-Sac fragment of BT-R$_1$ is capable of binding Cry1Ab insecticidal toxin.

To further understand the nature of this binding site, a set of truncation mutants of BT-R$_1$ was prepared through the use of restriction digests. The cDNA was digested at specific sites to remove increasingly larger portions of the C-terminus. The restriction enzymes used were NsiI, BamHI, NruI, ClaI, XhoI and StuI (FIGS. 1 and 3). The procedure involved linearizing the plasmid at each one of these sites and transcribing up to the truncation. The shortened mRNAs then were translated in an RRL kit blotted to nitrocellulose and hybridized with $^{125}$I-labeled Cry1Ab. Translation of the wild-type BT-R$_1$ from the cDNA showed binding to a 172-kDa protein band, the expected size of wild-type BT-R$_1$. It also shows smaller bands that bind Cry1Ab although the nature of these bands has not been determined. A blank made by preparing an RRL reaction mixture without any mRNA gaves several bands below 66 kDa that show some type of binding of Cry1Ab to the reticulocytes. The specificity of this binding has not been determined. The truncation mutants created by NsiI, BamHI, NruI, ClaI, XhoI and StuI restriction digests did not show any binding to Cry1Ab except in the region where the reticulocytes bind CR1Ab. This data demonstrates that the removal of the last 100 amino acids from wild type BT-R$_1$ by NsiI restriction results in the loss of the ability of BT-R$_1$ to bind Cry1Ab. This localizes the toxin binding site on the BT-R$_1$ clone and provides a soluble fragment of the receptor that can be used in toxin and other binding studies.

Figure 8:
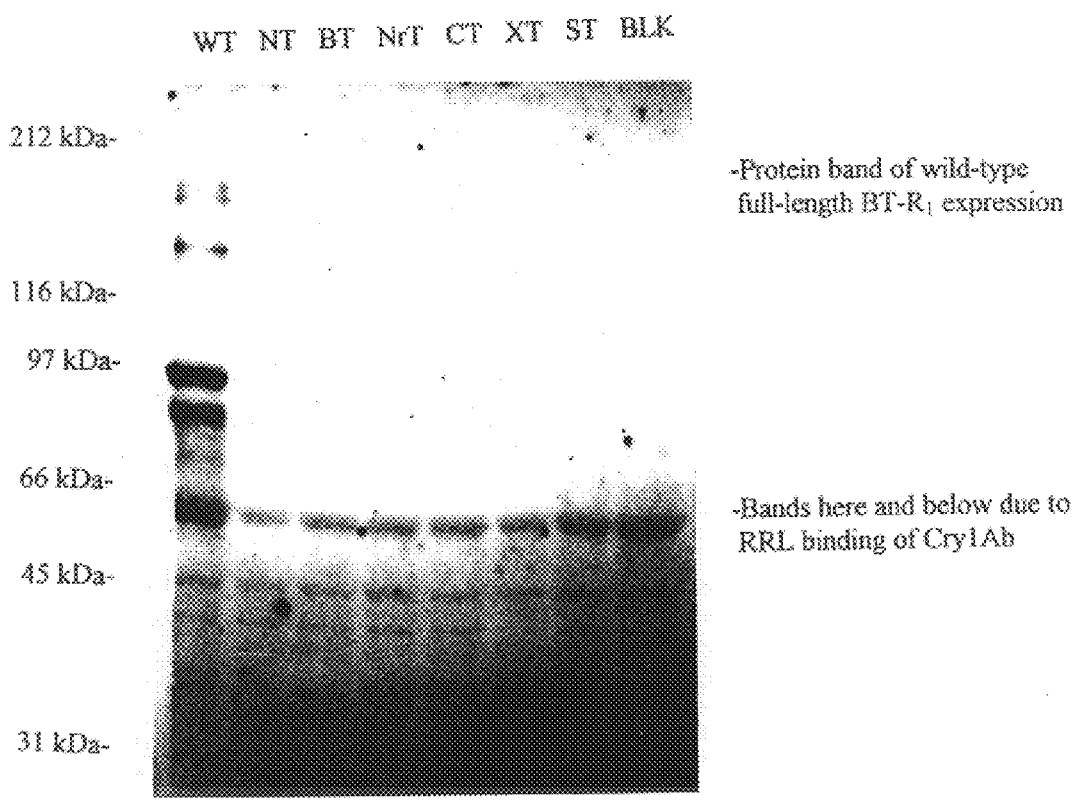
FIG. 8 shows the binding of Cry1Ab to fragments of the BT-$R_1$ protein.

A clone of a fragment of BT-R$_1$, called the Bam-Sac fragment, has been prepared. It was prepared using BamHI and SacI restriction digests (FIG. 1) and cloning of the resulting fragment into a vector called pCITE. The polypeptide sequence was translated and tested for binding to the insecticidal toxin Cry1Ab (FIG. 8). The Bam-Sac fragment binds to Cry1Ab, providing first insight into the location of the Cry1Ab binding site within the BT-R$_1$ sequence. It lies in the last 234 C-terminal amino acids. This evidence is further supported by a set of truncation mutants that has been prepared. Removal of the 100 most C-terminal amino acids from wild type BT-R$_1$ results in the loss of Cry1Ab binding. The C-terminal end of BT-R$_1$ is the location of the Cry1Ab binding site.

EXAMPLE 6

Identification of Homologue of BT-R$_1$ that Binds to a BT Toxin

Figure 7A:
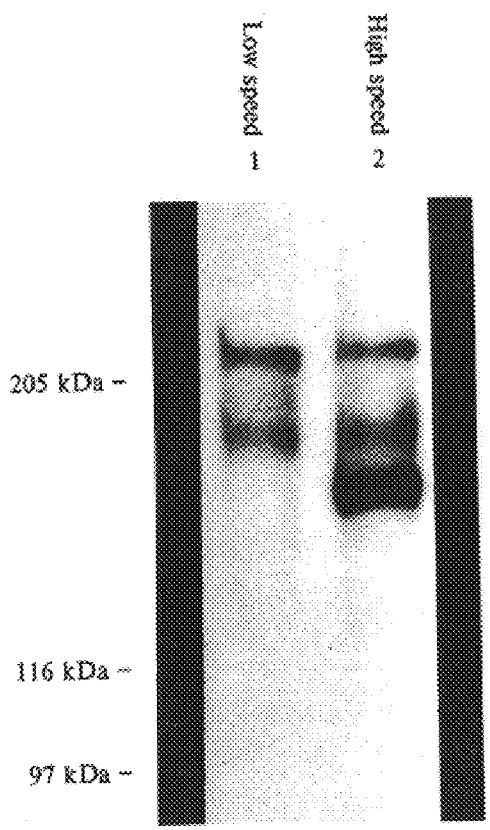
FIG. 7 shows the presence of a BT-$R_1$ homologue in Pink Bollworm and European Corn Borer identified using toxin binding similar to that used to identify the original BT-$R_1$ clone.
Figure 7B:
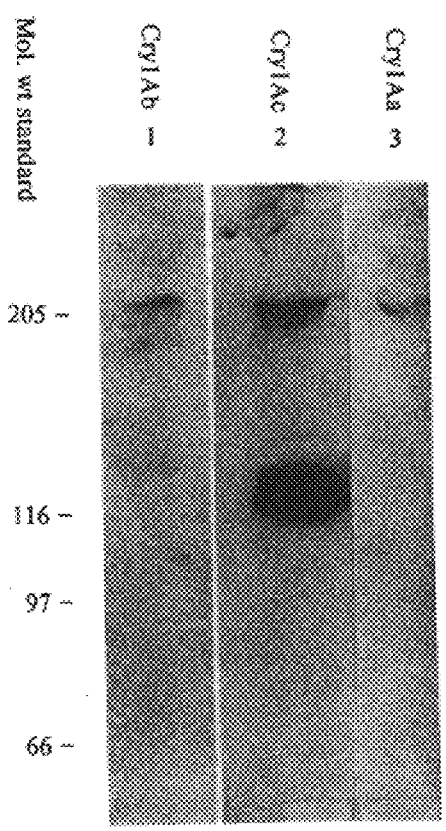

Western blots of tissue extracts prepared from Pink bollworm and European corn borer were prepare and probed with labeled Cry1a (FIG. 7). The results show that homologues of BT-R$_1$ are present in these two insects and can be readily isolated using the methods described herein.

What is claimed is:

1. A method to identify agents that block the binding of a BT-toxin to a BT-toxin receptor, said method comprising the steps of:
   (i) contacting an agent, in the presence and absence of a BT-toxin, to a BT-toxin binding receptor or cell expressing said receptor selected from the group consisting of:
      (a) a cell that has been altered to contain a nucleic acid molecule that encodes a BT-toxin receptor having the amino acid sequence of SEQ ID NO:2 and expresses said receptor;
      (b) a cell that has been altered to contain a nucleic acid molecule that encodes a BT-toxin receptor, wherein said nucleic acid molecule hybridizes to the polynucleotide sequence of SEQ ID NO:1 under stringent conditions, wherein said cell expresses said receptor and wherein said receptor is obtainable from an insect;
      (c) a cell that has been altered to contain a nucleic acid molecule encoding a BT-toxin receptor, wherein said nucleic acid molecule hybridizes to the polynucleotide sequence of SEQ ID NO:1 under stringent conditions, wherein said cell expresses the receptor and the receptor encoded by the nucleic acid binds to the CryIA(b) toxin;
      (d) an isolated BT-toxin receptor having an amino acid sequence of SEQ ID NO:2;
      (e) an isolated BT-toxin receptor that is encoded by a nucleic acid molecule that hybridizes to the polynucleotide sequence of SEQ ID NO:1 under stringent conditions, wherein said receptor is obtainable from an insect; and
      (f) an isolated BT-toxin receptor encoded by a nucleic acid molecule that hybridizes to the polynucleotide sequence of SEQ ID NO:1 under stringent conditions, wherein said receptor encoded by the nucleic acid binds to the CryIA(b) toxin;
   (ii) determining whether said agent blocks the binding of said BT-toxin to said BT-toxin receptor
   wherein the stringent conditions comprise:
      50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; or
      50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS; or
      0.015M NaCl, 0.0015M sodium citrate, and 0.1% SDS at 50° C.

2. The method of claim 1, wherein said BT-toxin is a member of the BT-cry(1) family of toxins.

3. The method of claim 1, wherein said cell that has been altered is a eukaryotic cell.

4. The method of claim 3, wherein said eukaryotic cell is an insect cell.

5. A method to identify agents that bind to a BT-toxin receptor, said method comprising the steps of:
   (i) contacting an agent with a BT-toxin binding receptor or cell expressing said receptor selected from the group consisting of:
      (a) a cell that has been altered to contain a nucleic acid molecule that encodes a BT-toxin receptor having the amino acid sequence of SEQ ID NO:2 and expresses said receptor;
      (b) a cell that has been altered to contain a nucleic acid molecule encoding a BT-toxin receptor, wherein said nucleic acid molecule hybridizes to the polynucleotide sequence of SEQ ID NO:1 under stringent conditions, wherein said cell expresses said receptor and wherein said receptor is obtainable from an insect;
      (c) a cell that has been altered to contain a nucleic acid molecule encoding a BT-toxin receptor, wherein said nucleic acid molecule hybridizes to the polynucleotide sequence of SEQ ID NO:1 under stringent conditions, wherein said cell expresses the receptor and the receptor encoded by the nucleic acid binds to the CryIA(b) toxin;
      (d) an isolated BT-toxin receptor having an amino acid sequence of SEQ ID NO:2;
      (e) an isolated BT-toxin receptor that is encoded by a nucleic acid molecule that hybridizes to the polynucleotide sequence of SEQ ID NO:1 under stringent conditions, wherein said receptor is obtainable from an insect; and
      (f) an isolated BT-toxin receptor encoded by a nucleic acid molecule that hybridizes to the polynucleotide sequence of SEQ ID NO:1 under stringent conditions, wherein said receptor encoded by the nucleic acid binds to the CryIA(b) toxin;
   (ii) determining whether said agent binds to said BT-toxin receptor;
   wherein the stringent conditions comprise:
      50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; or
      50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS; or
      0.015M NaCl, 0.0015M sodium citrate, and 0.1% SDS at 50° C.

6. The method of claim 5, wherein said method further comprises the step of determining whether said agent blocks the binding of a BT-toxin to said BT-toxin receptor.

7. The method of claim 5, wherein said cell that has been altered is a eukaryotic cell.

8. The method of claim 7, wherein said eukaryotic cell is an insect cell.

9. A method to produce a BT-toxin receptor protein, or a fragment thereof, said method comprising the steps of:

(i) culturing a cell that has been altered to contain a nucleic acid molecule that encodes a BT-toxin receptor protein, or BT-toxin binding fragment thereof, under conditions suitable for expression of said receptor protein or fragment thereof, wherein said cell has been altered to contain a nucleic acid molecule selected from the group consisting of:
  (a) a nucleic acid molecule that encodes the amino acid sequence of SEQ ID NO:2;
  (b) a nucleic acid molecule encoding a BT-toxin receptor, wherein said nucleic acid molecule hybridizes to the polynucleotide sequence of SEQ ID NO:1 under stringent conditions, and wherein said receptor is obtainable from an insect; and
  (c) a nucleic acid molecule encoding a BT-toxin receptor, wherein said nucleic acid molecule hybridizes to the polynucleotide sequence of SEQ ID NO:1 under stringent conditions, wherein the receptor encoded by the nucleic acid binds to the CryIA(b) toxin;
(ii) isolating said BT-toxin receptor protein or fragment;
wherein the stringent conditions comprise:

50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; or 50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS; or 0.015M NaCl, 0.001 5M sodium citrate, and 0.1% SDS at 50° C.

10. The method of claim 9, wherein said cell that has been altered is a eukaryotic cell.

11. The method of claim 10, wherein said eukaryotic cell is an insect cell.

* * * * *